US012582555B2

(12) United States Patent (10) Patent No.: US 12,582,555 B2
O'Shea et al. (45) Date of Patent: Mar. 24, 2026

(54) SYSTEMS AND METHODS OF PERFORMING TRANSCANAL EAR SURGERY

(71) Applicant: Stryker European Operations Holdings LLC, Portage, MI (US)

(72) Inventors: Conor O'Shea, Cahersiveen (IE); Damian Michael Curtin, Kerry (IE); Aidan Vaughan, Cork City (IE); Eoin Connolly, Dublin (IE)

(73) Assignee: Stryker European Operations Holdings LLC, Portage, MI (US)

( * ) Notice: Subject to any disclaimer, the term of this patent is extended or adjusted under 35 U.S.C. 154(b) by 1324 days.

(21) Appl. No.: 16/981,562

(22) PCT Filed: Apr. 12, 2019

(86) PCT No.: PCT/US2019/027223
§ 371 (c)(1),
(2) Date: Sep. 16, 2020

(87) PCT Pub. No.: WO2019/200259
PCT Pub. Date: Oct. 17, 2019

(65) Prior Publication Data
US 2021/0059859 A1 Mar. 4, 2021

Related U.S. Application Data

(60) Provisional application No. 62/657,281, filed on Apr. 13, 2018.

(51) Int. Cl.
*A61F 11/20* (2022.01)
*A61B 1/018* (2006.01)
(Continued)

(52) U.S. Cl.
CPC .............. *A61F 11/20* (2022.01); *A61B 1/018* (2013.01); *A61B 1/227* (2013.01); *A61B 1/32* (2013.01);
(Continued)

(58) Field of Classification Search
CPC ........... A61F 11/20; A61B 2017/00787; A61B 2217/005; A61B 2217/007;
(Continued)

(56) References Cited

U.S. PATENT DOCUMENTS 4,024,866 A 5/1977 Wallach
4,441,485 A * 4/1984 Reynolds ............... A61B 90/00
269/1
(Continued)

FOREIGN PATENT DOCUMENTS

CN 202459544 U 10/2012
CN 104379097 A 2/2015
(Continued)

OTHER PUBLICATIONS

English language abstract for CN 104379097 A extracted from espacenet.com database on Nov. 1, 2022, 2 pages.
(Continued)

*Primary Examiner* — Darwin P Erezo
*Assistant Examiner* — Raihan R Khandker
(74) *Attorney, Agent, or Firm* — Howard & Howard Attorneys PLLC

(57) ABSTRACT

Systems and methods for performing transcanal ear surgery. A volume of fluid is maintained within the ear canal to provide a flooded environment. A cutting member of a cutting instrument is submerged and operated within the flooded environment to resect tissue within the ear. A reservoir system may be coupled to the patient to facilitate providing the flooded environment. The reservoir system at
(Continued)

least partially surrounds the auricle of the ear in fluid-tight sealing engagement with the head of the patient. An irrigation pump and a suction source on one or both of the reservoir system and the cutting instrument are operated to provide the flooded environment. The reservoir system includes an access opening sized to receive one or more surgical instruments, for example, the cutting instrument and an endoscope. The flooded environment improves cooling of the surgical site and visualization of the surgical site from the endoscope.

17 Claims, 13 Drawing Sheets

(51) Int. Cl.

| | |
|---|---|
| *A61B 1/227* | (2006.01) |
| *A61B 1/32* | (2006.01) |
| *A61B 17/00* | (2006.01) |
| *A61B 17/3207* | (2006.01) |

(52) U.S. Cl.
CPC .............. *A61B 17/320758* (2013.01); *A61B 2017/0034* (2013.01); *A61B 2217/005* (2013.01); *A61B 2217/007* (2013.01)

(58) Field of Classification Search
CPC .... A61B 17/320758; A61B 2017/0034; A61B 1/018; A61B 1/227; A61B 1/32; A61M 39/06; A61M 39/02; A61M 2039/062; A61M 2039/0626
See application file for complete search history.

(56) References Cited

U.S. PATENT DOCUMENTS

| | | | |
|---|---|---|---|
| 5,707,383 | A | 1/1998 | Bays et al. |
| 5,749,099 | A | 5/1998 | Voorhees |
| 5,916,150 | A | 6/1999 | Sillman |
| 5,944,711 | A | 8/1999 | Pender |
| 6,024,720 | A | 2/2000 | Chandler et al. |
| 6,152,941 | A | 11/2000 | Himes et al. |
| 6,440,102 | B1 | 8/2002 | Arenberg et al. |
| 6,689,146 | B1 | 2/2004 | Himes |
| 7,238,010 | B2 | 7/2007 | Hershberger et al. |
| 7,621,898 | B2 | 11/2009 | Lalomia et al. |
| 7,717,931 | B2 | 5/2010 | Himes |
| 7,833,200 | B2 | 11/2010 | Viola |
| 8,172,846 | B2 | 5/2012 | Brunnett et al. |
| 8,216,199 | B2 | 7/2012 | Murray et al. |
| 8,475,481 | B2 | 7/2013 | Himes |
| 8,657,809 | B2 | 2/2014 | Schoepp |
| 8,718,795 | B2 | 5/2014 | Gibson |
| 8,740,866 | B2 | 6/2014 | Reasoner et al. |
| 8,915,897 | B2 | 12/2014 | Murray et al. |
| 9,028,398 | B2 | 5/2015 | Kumar et al. |
| 9,233,193 | B2 | 1/2016 | Truckai et al. |
| 9,364,648 | B2 | 6/2016 | Girotra et al. |
| 9,579,428 | B1 | 2/2017 | Reasoner et al. |
| 9,901,407 | B2 | 2/2018 | Breisacher et al. |
| 10,028,644 | B2 | 7/2018 | Konstorum et al. |
| 2004/0102770 | A1 | 5/2004 | Goble |
| 2007/0261494 | A1* | 11/2007 | Fuller .................... A61B 8/445 73/620 |
| 2009/0028356 | A1 | 1/2009 | Ambrose et al. |
| 2009/0036918 | A1 | 2/2009 | Burgess |
| 2009/0082634 | A1 | 3/2009 | Kathrani et al. |
| 2009/0270894 | A1* | 10/2009 | Rubin .................... A61M 1/842 600/156 |
| 2009/0270899 | A1 | 10/2009 | Carusillo et al. |
| 2010/0234867 | A1 | 9/2010 | Himes |
| 2011/0301572 | A1 | 12/2011 | Vlodaver et al. |
| 2012/0172888 | A1* | 7/2012 | Shugrue ................. A61B 1/303 606/119 |
| 2013/0023914 | A1* | 1/2013 | Truong .................. A61B 1/015 606/162 |
| 2013/0131580 | A1 | 5/2013 | Blackhurst et al. |
| 2014/0135617 | A1 | 5/2014 | Schoepp |
| 2014/0243658 | A1 | 8/2014 | Breisacher et al. |
| 2016/0089184 | A1 | 3/2016 | Truckai et al. |
| 2017/0040012 | A1 | 2/2017 | Goldstein |
| 2017/0296388 | A1 | 10/2017 | Gaynes et al. |
| 2017/0354431 | A1 | 12/2017 | Rubin et al. |

FOREIGN PATENT DOCUMENTS

| | | |
|---|---|---|
| CN | 207012294 U | 2/2018 |
| JP | 2007521916 A | 8/2007 |
| WO | 2006076708 A2 | 7/2006 |
| WO | 2016054140 A1 | 4/2016 |
| WO | 2016122500 A1 | 8/2016 |
| WO | 2016182999 A1 | 11/2016 |

OTHER PUBLICATIONS

English language abstract for JP 2007-521916 A extracted from espacenet.com database on Mar. 10, 2023, 2 pages.

English language abstract and machine-assisted English translation for CN 202459544 U extracted from espacenet.com database on May 25, 2023, 7 pages.

English language abstract and machine-assisted English translation for CN 207012294 U extracted from espacenet.com database on May 25, 2023, 5 pages.

English language abstract and original Chinese language document for "A Report of 316 Cases of Neuroendoscopic Surgery in Water Environment", Apr. 30, 2007, pp. 757-759, 1 page abstract.

International Search Report for Application No. PCT/US2019/027223 dated Aug. 9, 2019, 1 page.

Alexander, Milton et al., "Anthropometry of the Human Ear (A Photogrammetric Study of USAF Flight Personnel)", Jan. 1968, 38 pages.

Abstract of Grewe, Johanna et al., "New HRCT-Based Measurement of the Human Outer Ear Canal as a Basis for Acoustical Methods", Am J Audiol., vol. 22, No. 1, pp. 65-73, Jun. 2013, 1 page.

Kakehata, Seiji et al., "Extension of Indications for Transcanal Endoscopic Ear Surgery Using an Ultrasonic Bone Curette for Cholesteatomas", Otology & Neurotology, vol. 35, pp. 101-107.

Abstract of Kakehata, Seiji et al., "Powered Endoscopic Ear Surgery", Practica Oto-Rhino-Laryngologica, vol. 106, No. 3, pp. 187-199, 2013, 3 pages.

Abstract of Ito, Tsukasa, "Transcanal Endoscopic Ear Surgery for Lateralized Tympanic Membrane and Medial Meatal Fibrosis", vol. 130, Supplement S3 (Abstracts for the 10th International Conference on Cholesteatome), May 2016, p. S149.

Medtronic, "Visao Otologic Drill Webpage", 2020, 5 pages.

Shanks & Lily, Ear Canal Volume Chart, 1981, 1 page.

Stepp, Cara E. et al., "Acoustics of the Human Middle-Ear Air Space", May 26, 2005, 11 pages.

* cited by examiner

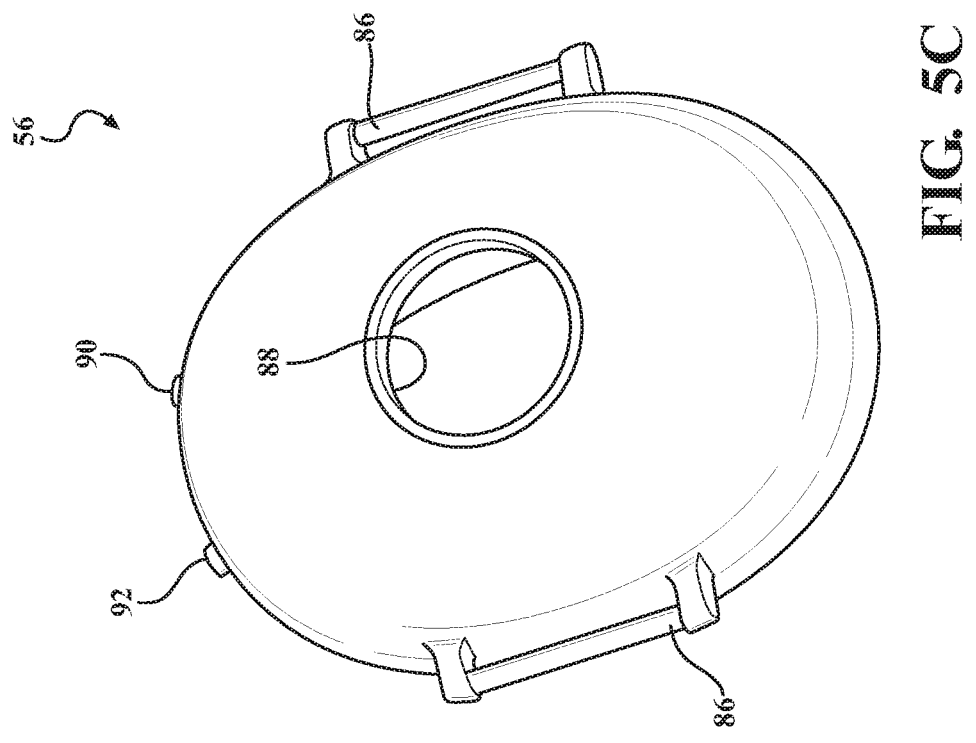
FIG. 5C
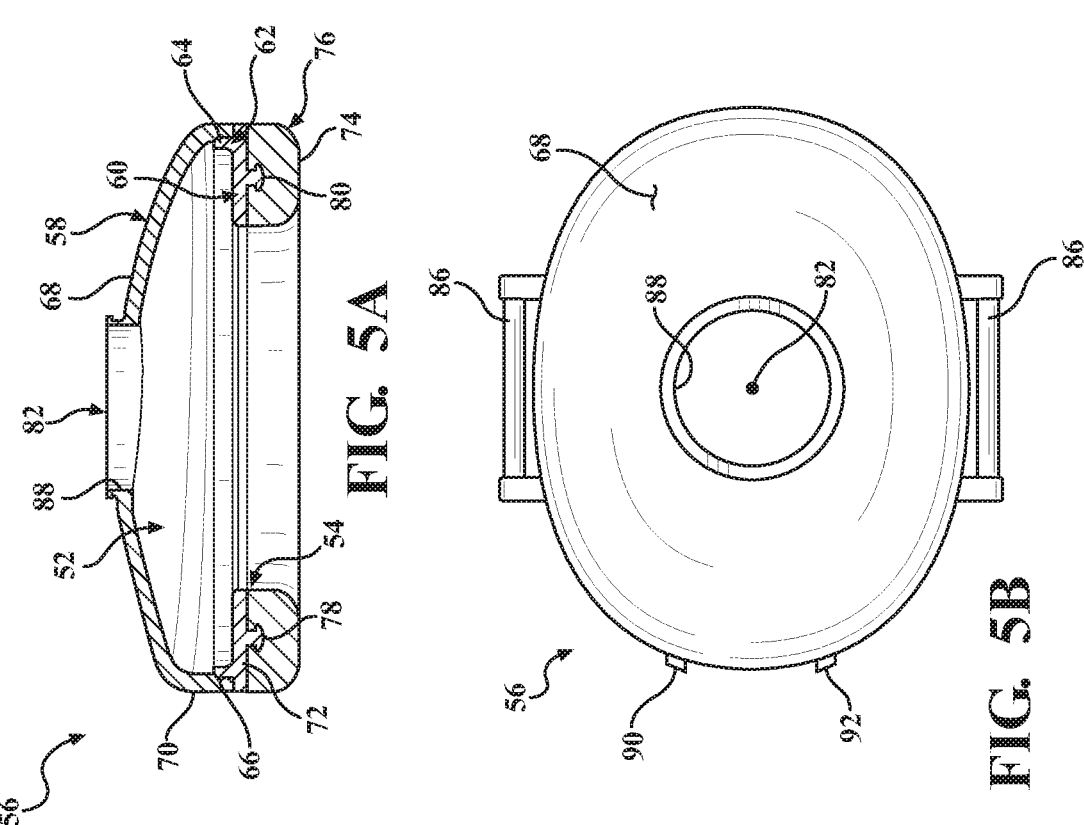
FIG. 5A
FIG. 5B

SYSTEMS AND METHODS OF PERFORMING TRANSCANAL EAR SURGERY

CROSS-REFERENCE TO RELATED APPLICATIONS

This application is a United States national entry of International Patent Application No. PCT/US2019/027223, filed on Apr. 12, 2019, which claims the benefit of and priority to U.S. Provisional Patent Application No. 62/657,281, filed on Apr. 13, 2018, the entire contents of each are hereby incorporated by reference in their entireties.

BACKGROUND

Many surgical procedures involve the resection of bone or tissue with a high-speed cutting instrument, often within small bodily orifices or cavities and/or through small incisions with limited visibility. The resection of the bone or tissue with the high-speed cutting instrument generates heat and debris. The generated heat increases the risk of necrosis or tissue damage, and the generated debris impairs the field of view at the surgical site. The problem of impaired visualization is prevalent in endoscopic procedures where the generated debris obstructs the field of view of the endoscope.

Of particular interest are endoscopic surgical procedures performed through the external auditory canal of the ear (i.e., the ear canal). In such a procedure, the endoscope improves visualization of the middle ear and the inner ear compared to an operative microscope. The surgeon supports the endoscope with one hand while performing tissue resection with an otologic cutting instrument within the field of view of the endoscope. Examples include resection of abnormal tissue growth such as a cholesteatoma, resection of the wall of the ear canal or temporal bone to improve access to the middle ear, and reducing the scutum (i.e., a sharp bony spur that is formed by the superior wall of the external auditory canal) during a tympanoplasty. FIG. 1 shows the human ear with certain structures and regions to be referenced in the present disclosure.

As with other surgical procedures using a high-speed cutting instrument within a small body cavity, the resection of the bone or tissue within the ear is associated with the generation of heat and the accumulation of debris. Known systems include providing irrigation and/or suction to clear the field of view and cool the cutting bur. Despite employing irrigation and/or suction, blood and bone debris may still obstruct the field of view. Furthermore, the risk of necrosis or tissue damage due to the elevated temperatures generated while resecting remains a prevalent challenge. Still further, the systems that provide irrigation and/or suction often require placement of additional instruments within the ear at the expense of valuable space within the ear canal.

Therefore, there is a need in the art for systems and methods for performing transcanal endoscopic ear surgery that overcome one or more of the aforementioned disadvantages.

BRIEF DESCRIPTION OF THE DRAWINGS

Advantages of the present disclosure will be readily appreciated as the same becomes better understood by reference to the following detailed description when considered in connection with the accompanying drawings.

FIG. 5 shows several views of a housing of the reservoir system of FIG. 2.

DETAILED DESCRIPTION

The present disclosure is generally directed to devices, systems, and methods for surgical procedures, and more specifically, but not exclusively, for surgical procedures performed through the ear canal of a patient, i.e., transcanal ear surgery.

Figure 1:
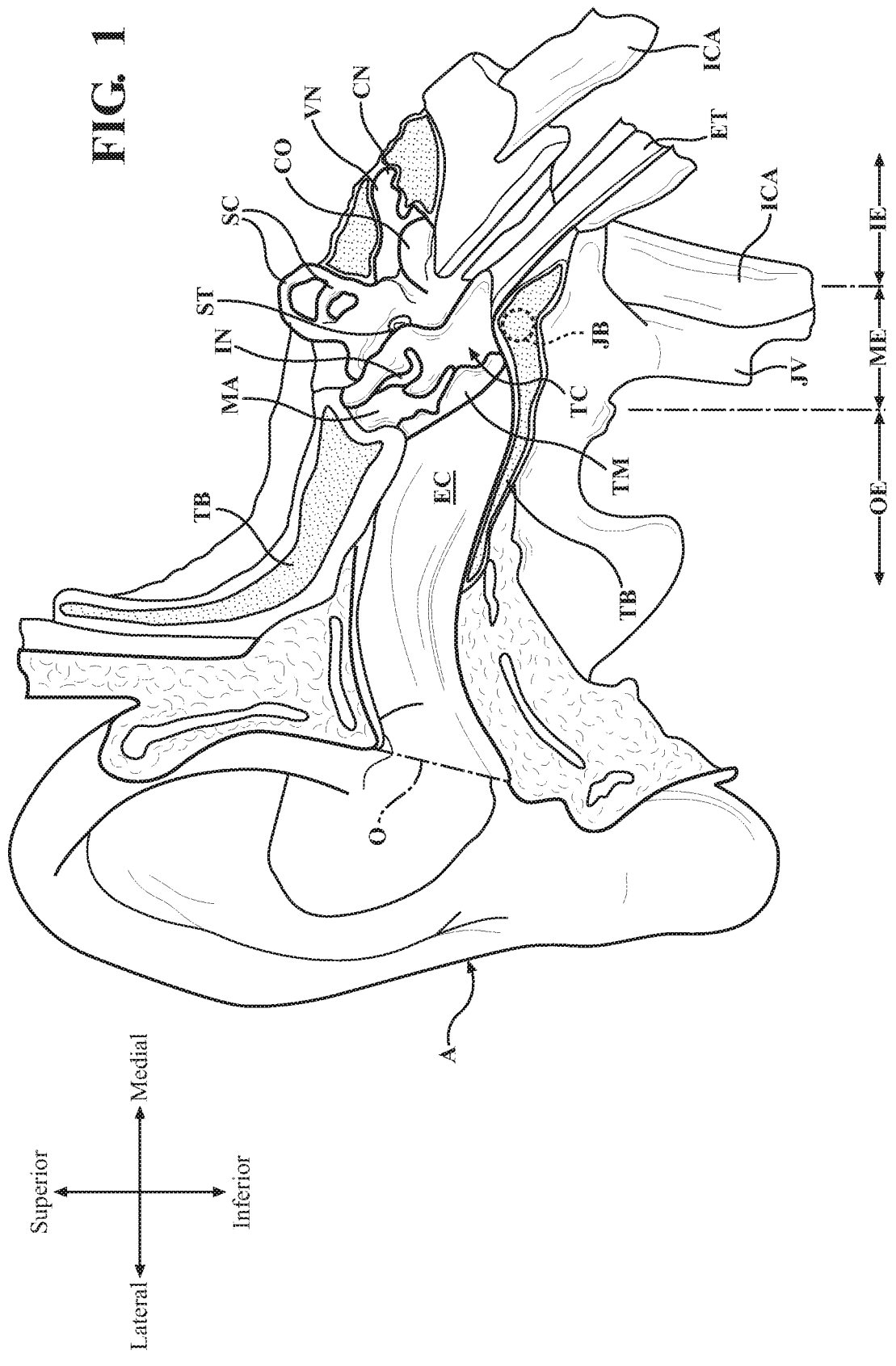
FIG. 1 is an illustration of a human ear identifying certain structures and regions.

FIG. 1 is an illustration of the human ear (right ear) with certain structures and regions to be referenced throughout the present disclosure. With reference to the compass rose of FIG. 1, it is noted that the anatomical directions will also be referenced in accordance with standard medical convention; i.e., medial to the center of the body, lateral to the side of the body, superior being above, and inferior being below. The human ear is generally divided into three regions, the inner ear (IE), the middle ear (ME), and the outer ear (OE). The inner ear is separated from the middle ear by a structure called the round window (not identified) with its mediolateral position generally approximated in FIG. 1. The inner ear includes structures such as the cochlea (CO), the vestibular nerve (VN), the cochlear nerve (CN), the Eustachian tube (ET), and the medial aspect of the internal carotid artery (ICA). It is noted that the Eustachian tube leads to the nasopharynx. Medial to the tympanic membrane is the tympanic cavity (TC) located within the middle ear. The middle ear further includes structures such as the malleus (MA), incus (IN), stapes (ST), semicircular canals (SC), the lateral aspect of the internal carotid artery, and a portion of the jugular vein (JV). A superior aspect of the jugular vein defines the jugular bulb to be discussed with the jugular bulb (JB) situated inferior to the tympanic cavity. The middle ear is separated from the outer ear by the tympanic membrane (TM), commonly known as the eardrum. The outer ear includes the external auditory canal, commonly known as the ear canal (EC). The auricle (A), commonly known as the earlobe, is external to the head (H) of the patient (see FIGS. 2-4). FIG. 1 shows the auricle and the ear canal separated by an opening (O) to be referenced in the present disclosure. Surrounding internal portions of the ear, for example, superior and inferior to the ear canal and the tympanic cavity, is temporal bone (TB). Of particular interest is the treatment of cholesteatomas, or abnormal growth within the ear often resulting in destruction of the portions of the temporal bone. One prominent location of cholesteatomas to be described in more detail is the superior aspect of the tympanic cavity near the tympanic membrane.

Figure 2:
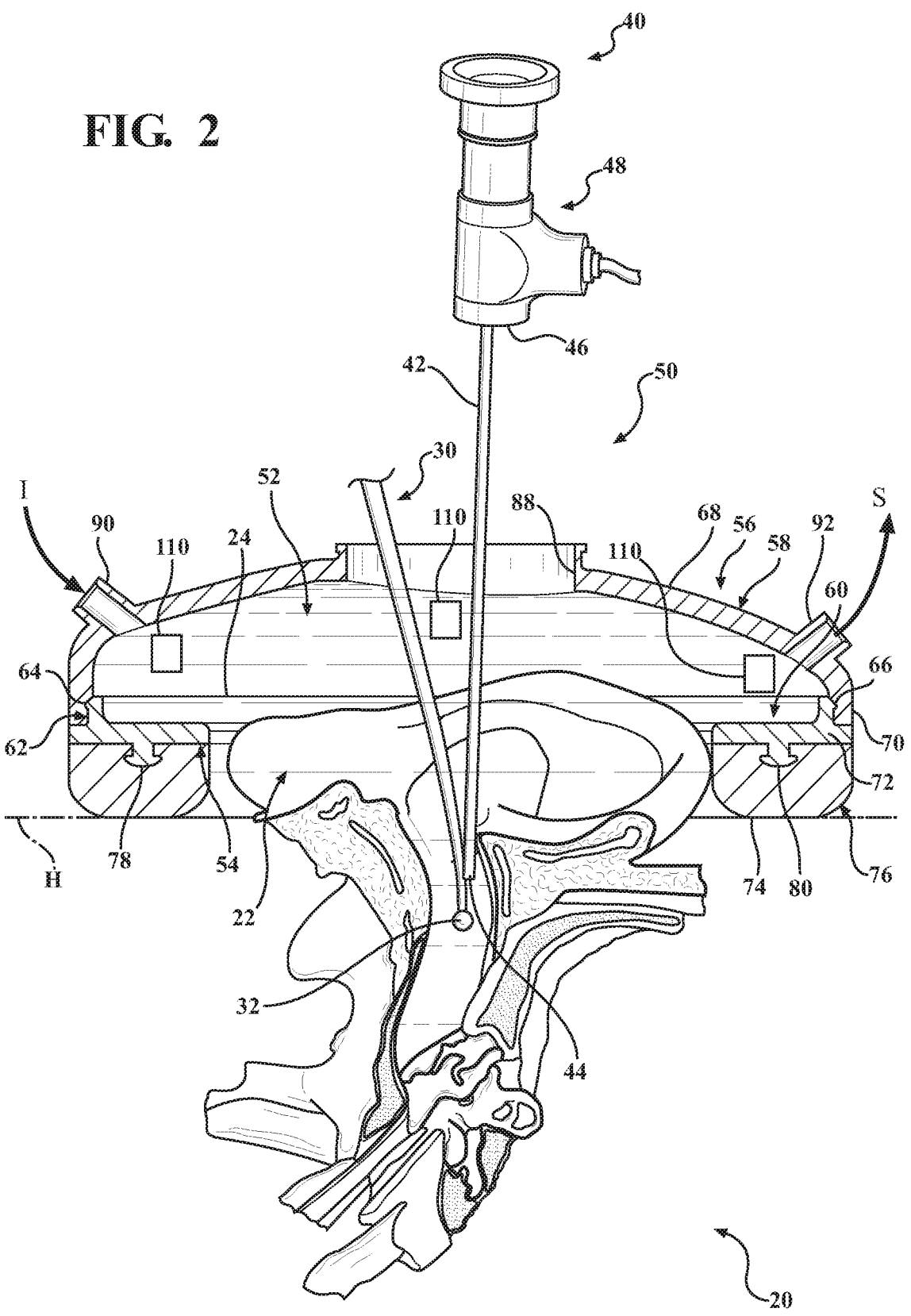
FIG. 2 is an illustration of a surgical system in accordance with an exemplary variation of the present disclosure with a reservoir system providing a flooded environment within the ear canal for performing a transcanal endoscopic surgical procedure with a cutting instrument.
Figure 3:
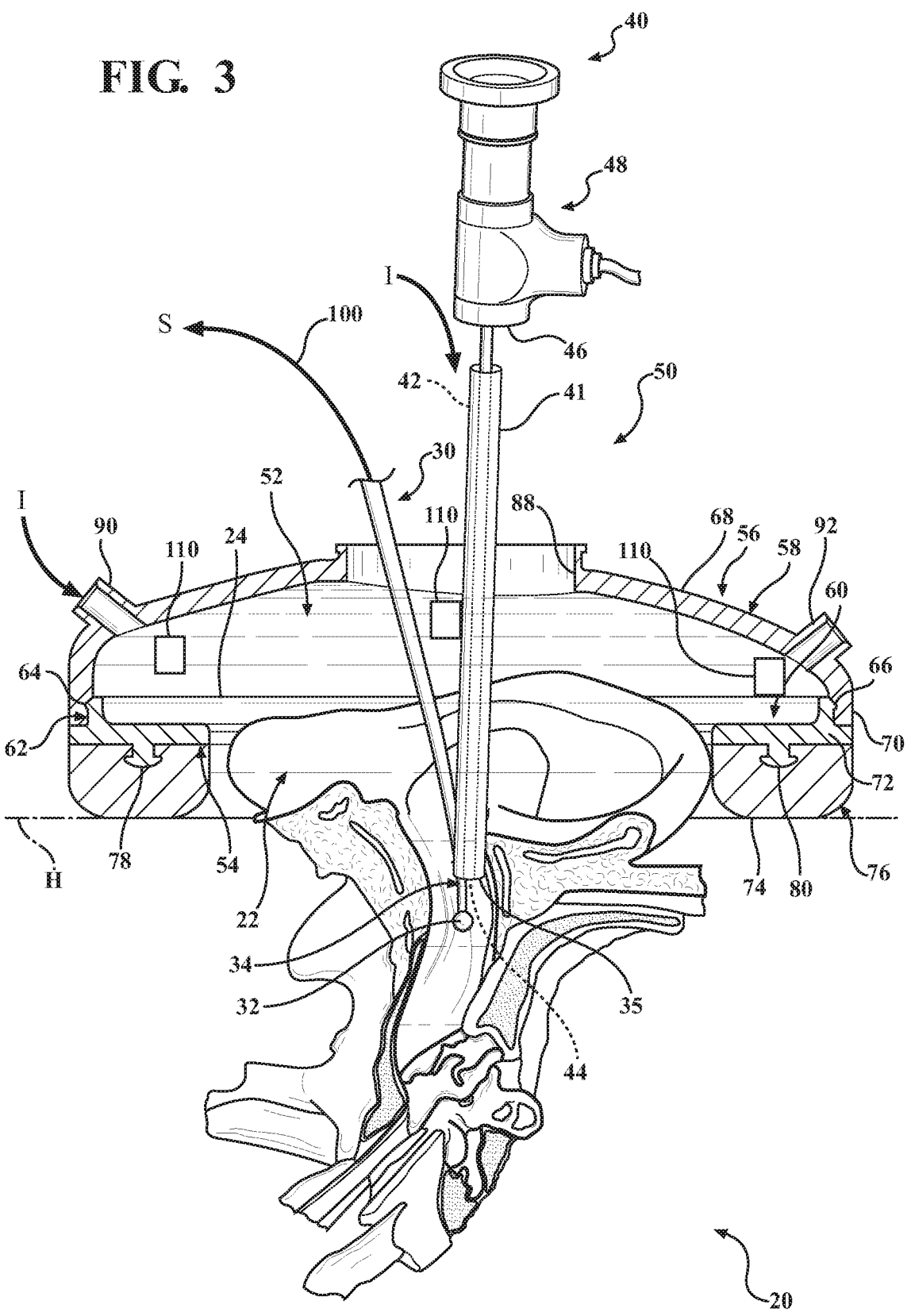
FIG. 3 is an illustration of the surgical system with a suction line associated with the cutting instrument to facilitate providing the flooded environment within the ear canal and the reservoir system for performing an endoscopic surgical procedure with the cutting instrument.
Figure 4:
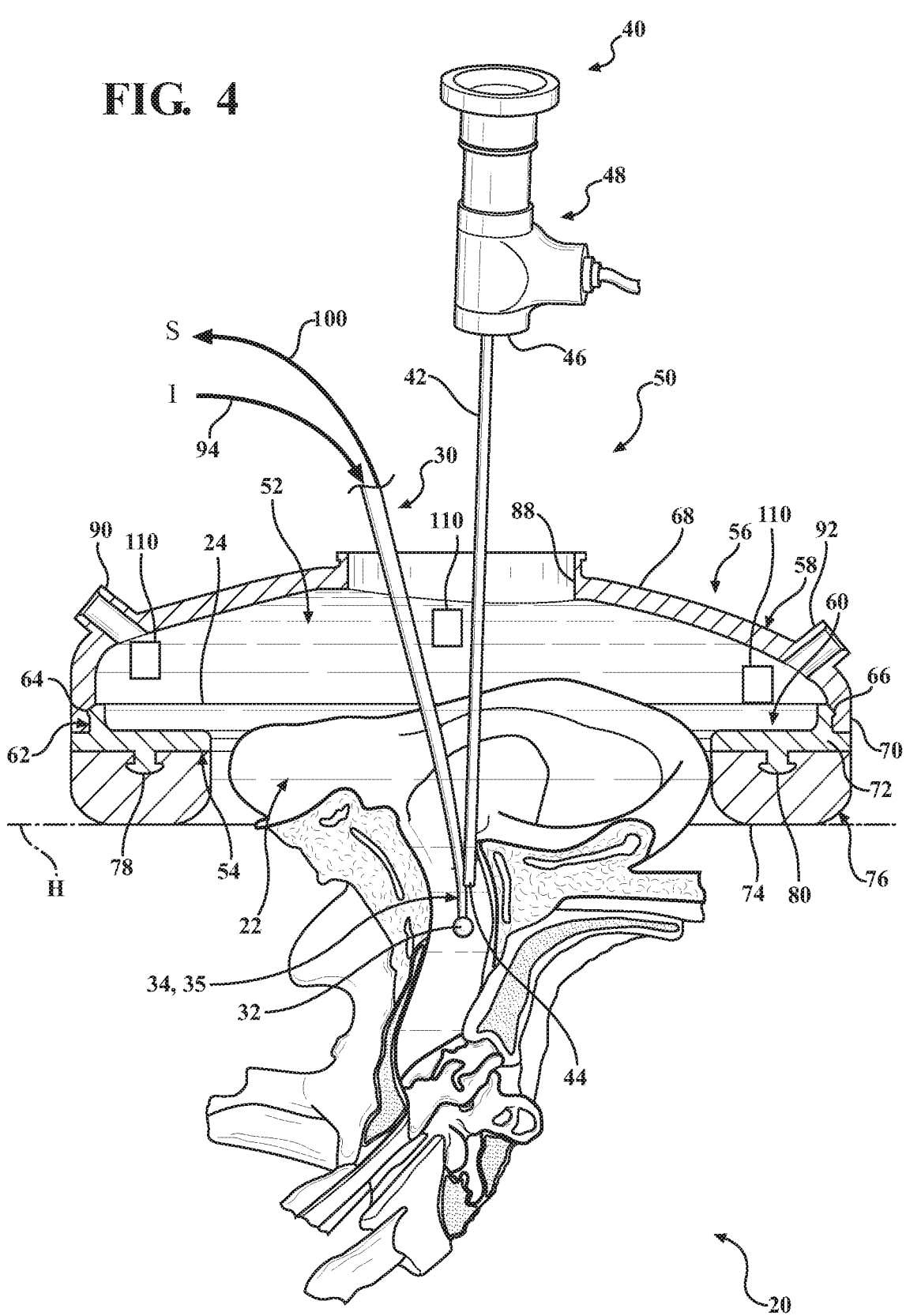
FIG. 4 is an illustration of the surgical system with the suction line and an irrigation line each associated with the cutting instrument to facilitate providing with the reservoir system the flooded environment within the ear canal and the reservoir system.

Known solutions of treating disorders of the ear through the ear canal include directing a manual surgical tool (e.g., a curette) or a powered surgical tool (e.g., a shaver or bur) to the site of the offending tissue, often under visualization from a microscope 126 or an endoscope 40. As mentioned, the resection of the bone or tissue with powered surgical tools is associated with the generation of heat and the accumulation of debris, which risks tissue damage and obstructs visualization, respectively. Known systems directing irrigation to the surgical site fail to provide adequate cooling and visualization. Referring now to FIGS. 2-4, a surgical system 20 in accordance with an exemplary variation of the present disclosure is shown. The surgical system 20 includes a cutting instrument 30, an endoscope 40, and a reservoir system 50 with each to be described in more detail. The reservoir system 50, and in certain variations the cutting instrument 30, provide a flooded environment 22 within the ear, and more particularly within the ear canal. Among other advantages, the flooded environment 22 may improve cooling of the cutting instrument 30 and the nearby tissue, and/or visualization of the surgical site from the endoscope 40.

The flooded environment 22 is provided with a suitable fluid, such as water, saline, and the like, preferably a liquid. The fluid is provided from a fluid source 98 (see FIG. 9) to within the ear. A volume of the fluid is maintained within the ear to provide the flooded environment 22. In particular, the fluid may be provided from the fluid source 98 to within the ear canal with the volume of the fluid maintained within the ear canal, as shown in FIGS. 2-4. The volume of the fluid providing the flooded environment 22 may vary by application, but it is generally sufficient to permit a cutting member 32 of the cutting instrument 30 to be partially or fully submerged. In one example, the volume of fluid is within the range of approximately 0.2 to 9 milliliters (mL), and more particularly within the range of approximately 0.35 to 6 mL, and even more particularly within the range of approximately 0.5 to 3 mL of fluid within the ear. Based on anthropomorphic data of the ear canal, it has been empirically determined that, for example, approximately 0.5 to 3 mL of the fluid within the ear canal provides sufficient volume for the cutting member 32 of the cutting tool 30 to be submerged. In another example, the fluid includes a fluid level 24 (e.g., a surface of the volume of the fluid) with the fluid level 24 being external to the ear canal or above the opening, as shown in FIGS. 2-4. In particular, FIGS. 2-4 show the fluid level 24 submerging the auricle. With the fluid level 24 external to the ear, an entirety of the ear canal is filled with the fluid to provide the flooded environment 22. It is understood, however, that not an entirety of the ear canal needs to be filled in certain aspects of the method. A portion of the ear canal, for example 20%, 30%, 40% or 50% or more of its length defined between the tympanic membrane and the opening (see FIG. 1), may be filled to provide the flooded environment 22.

In manners to be further described, providing the flooded environment 22 may include maintaining a steady state volume of the fluid within the ear canal. In certain variations, the fluid may be provided from the fluid source 98 at a flow rate, and suction may be provided to the flooded environment 22 at a suction rate substantially equal to the flow rate. With continued reference to FIGS. 2-4, providing the fluid from the fluid source 98 may be considered irrigation represented as (I), and providing the suction to the flooded environment 22 is represented as (S). FIG. 2 shows the reservoir system 50 providing the irrigation and the suction; FIG. 3 shows the reservoir system 50 providing the irrigation and the cutting instrument 30 providing the suction; and FIG. 4 shows the cutting instrument 30 providing the irrigation and the suction. It is contemplated that, in certain variations, the cutting instrument 30 provides the irrigation and the reservoir system 50 provides the suction. The endoscope 40 may provide the irrigation and/or the suction as well.

In certain variations, the irrigation and the suction may be performed simultaneously and continuously during the surgical procedure. For example, should the suction rate be substantially equal to the flow rate, it may be desirable to perform the irrigation and suction simultaneously and continuously to maintain the steady state volume. In certain other variations, the irrigation may be performed at the flow rate and the suction at the suction rate unequal to the flow rate such that the volume of the fluid within the ear canal and reservoir is variable. In still other configurations, the irrigation may be performed at the flow rate and the suction at the suction rate unequal to the flow rate, but with the volume of the fluid within the ear canal remaining substantially steady state. For example, the irrigation or suction with the higher of the flow rate and the suction rate may be performed intermittently while the other is performed continuously. In such an example, the intermittent irrigation or suction at the higher rate results substantially offsets the continuous irrigation or suction at the lower rate over a sufficient period of time; e.g., one, two or three or more minutes, or the duration of the surgical procedure. It is contemplated that in certain variations, the flow rate and/or the suction rate may be within the range of approximately 5 to 100 milliliters per minute (mL/min), and more particularly within the range of approximately 5 to 50 mL/min, and even more particularly within the range of approximately 5 to 30 mL/min. A default flow rate and/or suction rate, which may be selectively changed, may be set at approximately 14 mL/min. Other alternatives for maintaining the steady state volume are contemplated.

With the flooded environment 22 provided within the ear canal, the cutting member 32 of the cutting instrument 30 is submerged within the flooded environment 22. As used herein, submerged means to be positioned within the volume of fluid and/or positioned beneath the fluid level. The cutting instrument 30 is operated to rotate the cutting member 32 within the flooded environment 22 to resect tissue within the ear. For cutting instruments 30 with the cutting member 32 including a bur head (see FIGS. 10 and 11), the method may include submerging the entirety of the bur head and only a portion of the drive shaft coupled to the bur head. The benefits of performing the tissue resection within the flooded environment 22 are readily realized with the nearly an entirety of the cutting member 32 and the surrounding tissue being in direct contact with the fluid, thereby maximizing heat transfer to the fluid. Potential elevation of the temperature of the cutting member 32 and the surrounding tissue is limited, which may improve cutting efficiency of the cutting member 32 and/or lessen the likelihood of surrounding tissue damage.

With continued reference to FIGS. 2-4, a distal end 44 of the endoscope 40 may be submerged within the flooded environment 22. One exemplary endoscope suitable for the present application is the 1188 HD 3-Chip Camera manufactured by Stryker Corporation (Kalamazoo, Mich.). It is also contemplated that a microscope 126 may be used in lieu of the endoscope 40 as will be described below with reference to FIG. 10. The endoscope 40 of FIGS. 2-4 includes a shaft 42 defined between the distal end 44 and a proximal end 46 opposite the distal end 44. The proximal end 46 of the shaft 42 may be coupled to a handpiece 48 adapted to be grasped and manipulated by a physician. The distal end 44 of the shaft 42 is submerged within the flooded environment 22. In certain configurations, the cutting instrument 30 may be operated to rotate the cutting member 32 within the field of view of the endoscope 40 during at least a portion of the surgical procedure. With the irrigation and suction being provided to the flooded environment 22, the fluid exchange minimizes obstruction of the field of view of the endoscope 40, further realizing the benefits of performing the tissue resection within the flooded environment 22. For example, with the irrigation and suction being provided, especially to the volume of fluid maintained in the reservoir system 50, a swirling effect may result that moves debris away from the field of view of the endoscope 40.

In certain configurations, the reservoir system 50 facilitates providing the flooded environment 22. However, it should be appreciated that certain methods contemplated throughout this disclosure may be performed without the reservoir system 50. With continued reference to FIGS. 2-4 and further reference to FIG. 5, the reservoir system 50 is configured to be coupled to the head of a patient (see also FIGS. 8A and 8B). The reservoir system 50, in its most general sense, is arranged in a substantially fluid-tight sealing engagement with the head of the patient to provide a fluid reservoir volume 52 to accommodate the volume of the fluid constituting the flooded environment 22. The reservoir system 50 is configured to be coupled to the head of the patient in a non-invasive manner. As shown in FIGS. 2-5, the reservoir system 50 includes an opening 54 sized to receive the auricle of the ear such that the reservoir system 50 at least partially, and in certain variations, entirely encircles or surrounds the auricle. With the reservoir system 50 surrounding and further extending above the auricle, the fluid reservoir volume 52 accommodates additional fluid beyond the entirety of the ear canal being filled with the fluid. In other words, the flooded environment 22 may include the fluid filling the entirety of the ear canal and additional fluid within the fluid reservoir volume 52 above the ear.

The reservoir system 50 includes a housing 56. In the exemplary variation of the reservoir system 50 shown in FIGS. 2-5, the housing 56 includes an upper housing 58 and a lower housing 60. The upper and lower housings 58, 60 may be discrete and coupled structures, as shown in FIGS. 2-5, or integrally formed through injection molding or another suitable manufacturing process. The upper and lower housings 58, 60 in the illustrated variation are coupled together with coupling features associated with each of the upper and lower housings 58, 60. In particular, an annular flange 62 extends superiorly from the lower housing 60 with the annular flange 62 including an outwardly extending projection 64. The upper housing 58 includes an annular groove 66 extending circumferentially within an inner surface. The annular groove 66 receives the projection 64 to provide an interference fit between the upper and lower housings 58, 60. Other joining means are contemplated, for example bonding (e.g., solvent or adhesive), welding (e.g., heat or ultrasonic), fasteners (e.g., screws, bolts, or rivets), and the like. The upper housing 58, and in the illustrated variation the lower housing 60, at least partially defines the fluid reservoir volume 52 therebetween.

The upper housing 58 may be defined between a superior aspect 68 and a lateral aspect 70. The superior aspect 68 may be generally considered an upper wall of the housing 56 with the lateral aspect 70 generally considered an upstanding sidewall of the housing 56. The superior and lateral aspects 68, 70 may be discrete and coupled structures, or integrally formed as shown in FIGS. 2-5. The superior and lateral aspects 68, 70 may be formed from rigid, semi-rigid, and/or compliant materials. The illustrated variation shows the superior and lateral aspects 68, 70 being suitably rigid such that the upper housing 58 maintains its shape, particularly when the volume of the fluid does not fully occupy the fluid reservoir volume 52. FIGS. 2-5 show the superior and lateral aspects 68, 70 collectively defining the upper housing 58 that is substantially hemispherical in shape such that the housing 56 substantially encapsulates the auricle. The lateral aspect 70 at least partially defines the opening 54 sized to receive the auricle of the ear. In certain variations where the upper housing 58 is formed from compliant materials, the housing 56 is generally conformable to the ear and the head of the patient. In one example, the housing 56 is configured to flex to form closely with the head of the patient. In another example, at least the upper housing 58 is highly flexible and unable to maintain its shape under its own weight. The profile of the housing 56 is reduced commensurate with the fluid level of the flooded environment 22. In other words, with no fluid provided to the ear canal, for example, the housing 58 may not maintain its shape and the superior and lateral aspects 68, 70 may generally rest upon the auricle of the ear under the influence of gravity. As sufficient fluid is provided such that the fluid level 24 is above the ear canal, the compliant upper housing 58 accommodates the fluid level 24.

The lateral aspect 70 and the superior aspect 68 at least partially define the fluid reservoir volume 52. In other words, the fluid reservoir volume 52 may be defined within a boundary defined by the lateral aspect 70, below the superior aspect 68, and above the opening of the ear. It is understood, however, that the superior aspect 68 of the housing 58 is optional in certain variations, and the lateral aspect 70 sufficiently extends above the ear to accommodate the flooded environment 22 (e.g., a cylindrical sidewall with no upper wall). In such an alternative variation, the fluid reservoir volume 52 may be defined within the boundary defined by the lateral aspect 70 and above the opening of the ear. It is further contemplated as an alternative to the upper housing 58 being substantially hemispherical or cylindrical, other shapes may include conic (i.e., frustum of a cone), rectangular, square, toroidal, higher-order polygons, and the like. Furthermore, the housing may assume other configurations not specifically contemplated herein.

Moreover, when viewed in plan (lower left illustration of FIG. 5), the housing 56 may be considered substantially elliptical with dimensions generally corresponding to those of the ear according to anthropomorphic data. For example, using known geometric conventions for ellipses, a semi-minor axis of the housing 56 may be within the range of approximately 20 to 60 millimeters (mm), and more particularly within the range of approximately 35 to 45 mm. A semi-major axis of the housing 56 may be within the range of approximately 30 to 70 mm, and more particularly within the range of approximately 40 to 60 mm. Based on anthropomorphic data of the auricle, it is been empirically determined that, for example, approximately 40 and 50 mm for the semi-minor and semi-major axes, respectively, provides sufficient volume to receive the auricle in the fluid-tight relationship with a flat portion of the head of surrounding the auricle. It is understood that the aforementioned dimensions may be varied based on anatomical dimensions of a particular application, including head size, ear size, shape of the auricle, and the like.

The lower housing 60 may define an inferior aspect 72. In the illustrated variation of FIGS. 2-5, the inferior aspect 72 further defines the fluid reservoir volume 52. The inferior aspect 72 is positioned opposite the superior aspect 68 such that the fluid reservoir volume 52 is collectively defined between the superior, lateral, and inferior aspects 68, 70, 72. The annular flange 62 extends superiorly from the inferior aspect 72 with the annular flange 62 adapted to engage the groove 64 to couple the upper and lower housings 58, 60. In certain variations to be later described (see FIGS. 6 and 7), the inferior aspect 72 is a portion of a unitary housing 56 not including separate upper and lower housings 58, 60. The inferior aspect 72 may at least partially define the opening 54 sized to receive the auricle of the ear. In particular, the inferior aspect 72 of FIGS. 2-5 is disc-shaped and at least partially defines the opening 54.

The reservoir system 50 may further include a sealing surface 74. The sealing surface 74, in a most general sense, is the interface between the reservoir system 50 and the head of the patient. In particular, the sealing surface 74 is positioned in an abutting relationship with the head about the auricle, as shown in FIGS. 2-5. The sealing surface 74, among other things, provides the fluid-tight seal or near-fluid tight seal between the reservoir system 50 and the head of the patient. With the housing 56 surrounding the auricle in the fluid-tight arrangement, the housing 56 maintains the volume of the fluid within the ear canal and the fluid reservoir volume 52 during the surgical procedure. In certain variations, the inferior aspect 72 defines the sealing surface 74 with the inferior aspect 72 being positioned in an abutting relationship with the head about the auricle. In the illustrated variation, the reservoir system 50 includes a sealing member 76 coupled to the inferior aspect 72 of the housing 56 with the sealing member 76 defining the sealing surface 74. The sealing member 76 may be formed from flexible, deformable, and/or conformable material(s) configured to provide the fluid-tight seal between the reservoir system 50 and the head of the patient. For example, the sealing member 76 may be an inflatable bladder adapted to receive fluid from a fluid source, or a gasket formed from a suitable material such as elastomeric rubber or silicone. The sealing member 76 may be coupled to the housing 56 through any suitable joining means, such as bonding, welding, fasteners, and the like. In the illustrated variation, barbs 78 extend inferiorly from the inferior aspect 72 of the lower housing 60. The sealing member 76 may include holes 80 sized such that the barbs 78 engage the holes 80 via friction or interference fit. It is further contemplated that a sealing agent (not shown) may be applied to the sealing surface 74 (or to the head of the patient to be in abutment with the sealing surface 74) to further improve the fluid-tight seal between the reservoir system 50 and the head of the patient. Exemplary sealing agents suitable for the present application include wax, gel, foam, mask seal, petroleum jelly, and the like.

The sealing member 74 at least partially defines the opening 54 sized to receive the auricle of the ear. With continued reference to FIGS. 2-5, the sealing member 74 is ring-shaped or toroidal and generally shaped to the inferior aspect 72 of the lower housing 60. In other words, with the sealing member 74 coupled to the inferior aspect 72, the sealing member 74 and the inferior aspect 72 may be coaxially arranged (about an axis extending through a pole 82 of the superior aspect 68) such that the sealing member 74 at least partially, and in certain variations entirely, encircles or surrounds the auricle.

Figures 8A, 8B:
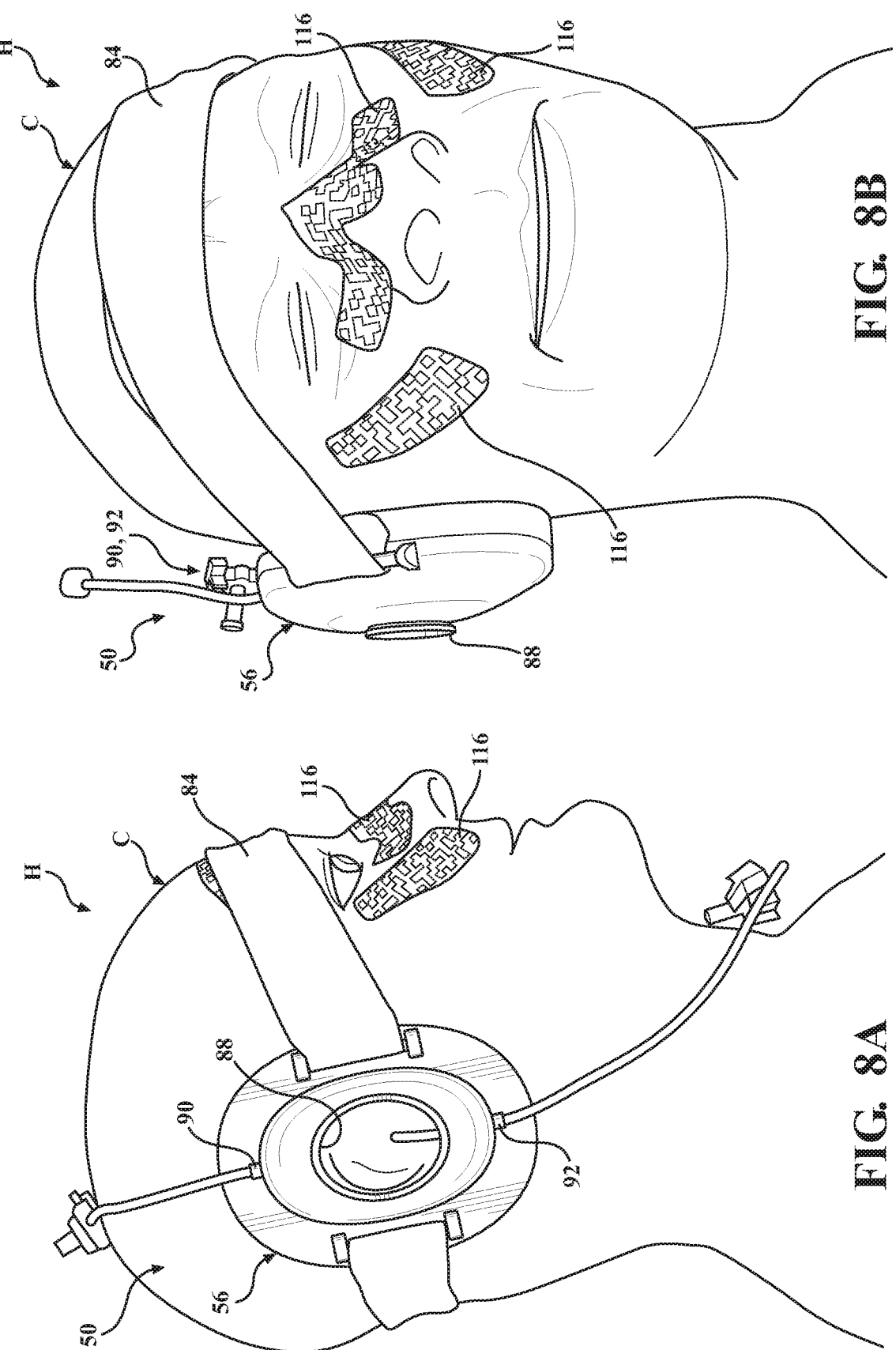
FIG. 8A is a perspective representation of the reservoir system coupled to the head of a patient positioned in the lateral decubitus position.
FIG. 8B is a perspective representation of the reservoir system of FIG. 8A coupled to the head of the patient positioned in the supine position.

The reservoir system 50 may further include a retention feature 84 configured to facilitate maintaining the fluid-tight seal between the reservoir system 50 and the head of the patient. The retention feature 84 is adapted to be coupled to the head of the patient, and more particularly to or about a cranium (C) of the head of the patient, as shown in FIGS. 8A and 8B. In the illustrated variation, the retention feature 84 is an elastic band coupled to the housing 56 and extending about the cranium of the patient. It is contemplated that the retention feature 84 may alternatively include a strap, adhesive, or other suitable means for coupling the retention system 50 to the head of the patient in the fluid-tight arrangement. FIG. 5 shows the housing 56 including coupling features 86 adapted to be removably coupled to the retention feature 84. The coupling features 86 of the illustrated variation include elongate posts coupled to an outer surface of the lateral aspect 70 of the upper housing 58. The elongate posts are configured to receive opposing ends (not shown) of the retention feature 84, for example, the elastic band. Other means for coupling the retention feature 84 and the housing 56 are contemplated, for example, buttons, snaps, zippers, clips, hook-and-eye connections, adhesives, knotting, and the like, disposed on one or both of the retention feature 84 and the housing 56. In other words, in certain configurations, the retention feature 84 is a non-invasive attachment device with no portion of the housing 56 penetrating the anatomy. The retention feature 84 provides for the sealing surface 74 arranged in flat-on-flat contact with the head of the patient surrounding the auricle and entirely external to the ear. However, it is also contemplated that the reservoir system 50 may be coupled to the head of the patient with an invasive retention device, such as one or more screws or pins.

Returning to FIGS. 2-5, the reservoir system 50 includes an access opening 88 defined within the superior aspect 68. The access opening 88 is suitably sized to receive one or more surgical instruments, for example, the cutting instrument 30 and/or the endoscope 40. For example, the access opening 88 may include a radius (centered on the axis extending through the pole 82) within the range of approximately 5 to 30 mm, and more particularly within the range of approximately 10 to 20 mm, and even more particularly approximately 15 mm. In the illustrated variation, the access opening 88 is a singular circular opening centered on the axis extending through the pole 82 of the superior aspect 68. In certain variations, the access opening 88 may be an ellipse with, for example, a semi-minor axis of approximately 20 mm and a semi-major axis of approximately 20 mm, and more particularly with the semi-minor axis of approximately 15 mm and a semi-major axis of approximately 20 mm. FIGS. 2-4 show both the cutting instrument 30 and the endoscope 40 simultaneously positioned through the access opening 88 and submerged in the flooded environment 22. It is contemplated that alternative size(s), shape(s), position(s), and combinations thereof, of one or more access openings 86 may be provided. For example, the access opening 88 may include two openings each extending through the superior aspect 68 with the openings off-centered and positioned opposite the pole 82. One of the one openings receives, for example, the cutting instrument 30, and the other one receives the endoscope 40. It is further contemplated that in variations without the superior aspect 68 (e.g., the cylindrical sidewall with no upper wall), the access opening 88 may be defined by the uppermost boundary of the lateral aspect 70.

A deflectable valve (not shown) may be coupled to the housing and disposed within the access opening 88. The deflectable valve prevents egress of the fluid from the fluid reservoir volume 52 through the access opening 88. In one example, the deflectable valve is a duckbill valve. In another example, the deflectable valve is a diaphragm formed from material (e.g., an elastomer) adapted to be impaled by the surgical instrument(s) and substantially maintain a seal between the valve and the impaling instrument(s). In such an example, the fluid reservoir volume 52 may be pressurized.

As mentioned, FIG. 2 shows the reservoir system 50 providing the irrigation and suction, schematically represented by (I) and (S), respectively, to maintain the volume of the fluid within the ear canal and provide the flooded environment 22. With concurrent reference to FIGS. 5 and 9, the reservoir system 50 may include one or more irrigation ports 90 and/or one or more suction ports 92. The irrigation port 90 is adapted to receive an irrigation line 94 in fluid communication with an irrigation pump 96 and the fluid source 98 to define an irrigation flow path, and the suction port 90 is adapted to be coupled to a suction line 100 in fluid communication with a suction source 102 and a disposal reservoir 104 or other disposal system to define a suction flow path. FIG. 5 shows the irrigation port 90 and the suction port 92 coupled to the housing 56, and more particularly to the lateral aspect 70 of the housing 56. The irrigation and suction ports 90, 92 are positioned on a same side of the housing 56, but other locations and arrangements are within the scope of the present disclosure (see FIG. 7). In one configuration, the suction port 92 may be positioned higher on the housing 56 than the irrigation port 90 to safeguard against overflow of the flooded environment 22. In configurations where the housing 56 has more than one irrigation ports 90 and/or suction ports 92, the irrigation ports 90 and/or suction ports 92 may be positioned on opposite sides of the housing, facilitating operation and maintaining the flooded environment 22 in the event that the housing is not level. The irrigation and suction ports 90, 92 are adapted to be removably coupled to the irrigation and suction lines 94, 100, respectively, with a Luer fitting, a bayonet mount, or other suitable connection providing fluid communication between the fluid reservoir volume 52 and the irrigation and suction paths.

In one example, the suction line 100, the suction source 102, and the disposal reservoir 104 are included in a surgical waste management system sold under the tradename NEP-TUNE manufactured by Stryker Corporation (Kalamazoo, Mich.) and disclosed in commonly owned U.S. Pat. Nos. 7,621,898; 8,216,199; 8,740,866; 8,915,897; 9,579,428, among others, each of which is hereby incorporated by reference in its entirety. The irrigation pump 96 and the suction source 102 are operably coupled to a controller 106 with the controller 106 adapted to control operation of the irrigation pump 96 and the suction source 102. Exemplary suction/irrigation systems are disclosed in U.S. Pat. No. 7,238,010, which is hereby incorporated by reference in its entirety. The system 50 may include one or more valves 108 disposed at suitable locations within the irrigation flow path and/or the suction flow path. The valves 108 are operably coupled to the controller 106 with the controller 106 adapted to control operation of the valves 108.

One or more sensors 110 to be described may be coupled to the housing 56 and operably coupled to the controller 106. The reservoir system 50 may further include a display 112 and a user input 114 each operably coupled to the controller 106. The display 112 may output parameters associated with the reservoir system 50, for example, the irrigation rate, the suction rate, the fluid level, the fluid volume, pressure level within the fluid reservoir volume 52, and/or combinations thereof. The user input 114 is configured to receive an input from a user to perform certain functions of the reservoir system 50, for example, turning the system on or off, increasing or decreasing the irrigation rate and/or the suction rate, and the like. The display 112 and user input 114 may be embodied on a mobile device such as a smartphone, tablet, or personal digital assistant (PDA), or on a laptop, desktop, or another suitable input-output device.

An exemplary operation of the reservoir system 50 may include positioning the patient in the lateral decubitus position (see FIG. 8A) to create a gravity well towards the middle ear of the patient. The reservoir system 50 is coupled to the head of the patient as described, for example, with the retention member 84. The controller 106 operates the irrigation pump 96 to direct the fluid from the fluid source 98 through the irrigation line 94 and the irrigation port 90, and operates the suction source 102 to draw suction through the suction port 92 and the suction line 100. The irrigation pump 96 and the suction source 102 may be operated in a manner such that the fluid level 24 is within the fluid reservoir volume 52 above the ear. In other words, the entirety of the ear canal is filled with the fluid, and the fluid further fills at least a portion of the housing 56 of the reservoir system 50. In the illustrated variation of FIG. 2, for example, the fluid level 24 is above the auricle and within the fluid reservoir volume 52 with the entirety of the ear canal filled with the fluid to provide the flooded environment 22. In one example, the controller 106 operates the irrigation pump 96 and the suction source 102 with the volume of fluid maintained within the ear canal and the fluid reservoir volume 52 to be within the range of approximately 10 to 750 mL, and more particularly within the range of approximately 20 to 500 mL, and even more particularly within the range of approximately 30 to 250 mL.

The one or more sensors 110 may be coupled to the housing 56 at suitable locations to detect the absence or presence of the fluid at the respective locations. In one variation, the aforementioned sensors 110 may include an electrical fluid sensing member coupled to the housing 56. The electrical fluid sensing member may be configured to sense impedance or resistance. In another variation, the sensors may further include a measurement vessel in communication with the housing 56 wherein the sensors 110 includes a pressure sensor configured to measure pressure within the measurement vessel. In yet another variation, the sensors 110 may be optical sensors to visually determine the presence of the fluid within the housing 56. The sensors 110 may transmit a fluid level signal to the controller 106, which in turn operates the irrigation pump 96 and/or the suction source 102 based on the fluid level signal to adjust or maintain the flooded environment 22 as desired.

In a certain variation, two or more sensors 110 may be coupled to the housing 56 at various locations of the housing 56, spaced across the ear canal. In this variation, the sensors 110 detect the absence or presence of the fluid at their respective locations and may transmit a fluid level signal to the controller 106. The controller 106, based upon the fluid level signal of the two or more sensors, may ascertain that the fluid level may be lower at one location of the housing 56 than another location of the housing 56. This variation provides the advantage of allowing the controller 106 to compensate for the housing 56 not being in a perfectly level position, such as positioned on the head of the patient, which may be slightly angled. In the event that the fluid level is lower at one sensor 110 that the other sensor(s) 110, the controller 106 can more accurately control the irrigation pump 96 and/or the suction source 102 based on the fluid level signal to adjust or maintain the flooded environment 22 as desired in the ear canal.

In certain exemplary operations, the controller 106 operates the irrigation pump 96 and the suction source 102 to maintain the steady state volume of the fluid within the ear canal and the fluid reservoir volume 52 such that an entirety of the ear canal is filled with fluid. The controller 106 operates the irrigation pump 96 to provide the fluid at the flow rate of the fluid and the suction source 102 to draw the fluid from the flooded environment 22 at the suction rate of the fluid based on the flow rate. In one example, the suction rate may be substantially equal to the flow rate with the irrigation and suction simultaneously and continuously. In another example, one of flow rate and the suction rate vary with one of the irrigation pump 96 and the suction source 102 being operated intermittently such that the net effect is that of equal volumes of fluid being provided to and removed from the fluid reservoir volume 52.

With the flooded environment 22 within the ear canal, and in certain variations within the fluid reservoir volume 52, one or more of the surgical instruments are directed through the access opening 88 of the housing 56. With continued reference to FIG. 2, the cutting member 32 of the cutting instrument 30 is directed through the access opening 88 and submerged in the flooded environment 22, and in certain variations, the distal end 44 of the endoscope 40 is directed through the access opening 88 and submerged in the flooded environment 22. The endoscope 40 may be directed through the access opening 88 while the cutting instrument 30 is positioned within the same access opening 88. In one example, the cutting instrument 30 is supported in one hand (of the physician) while the cutting member 32 is submerged within the flooded environment 22 through the access opening 88, and the endoscope 40 is supported in the other hand while the endoscope 40 is submerged within the flooded environment 22 through the access opening 88. With the cutting member 32 of the cutting instrument 30 submerged within the flooded environment 22, the cutting instrument 30 is operated to resect tissue within the ear. It is understood that in certain exemplary surgical methods, the cutting member 32 is submerged within the flooded environment 22 prior to resecting the tissue.

Several advantages of the reservoir system 50 may be realized from the foregoing disclosure. With the reservoir system 50 maintaining the flooded environment 22, particularly with the controller 106 operating the irrigation pump 96 and the suction source 102, the physician's attention may be appropriately focused on critical specifics of the surgical procedure; i.e., resecting the tissue within the ear. Furthermore, in certain configurations, the reservoir system 50 maintaining the flooded environment 22 obviates the need for introducing separate suction and irrigation tools into the ear canal, thereby preserving valuable space within the ear canal. Still further, as mentioned, the presence of the flooded environment 22 may improve cutting efficiency of the cutting member 32, lessen the likelihood of surrounding tissue damage, and/or minimize obstruction of the field of view of the endoscope 40. These advantages of the reservoir system 50 may be realized for example in several surgical procedures, such as tympanoplasty, stapedectomy, cochlear implant surgery, etc.

Figures 6A, 6B, 6C:
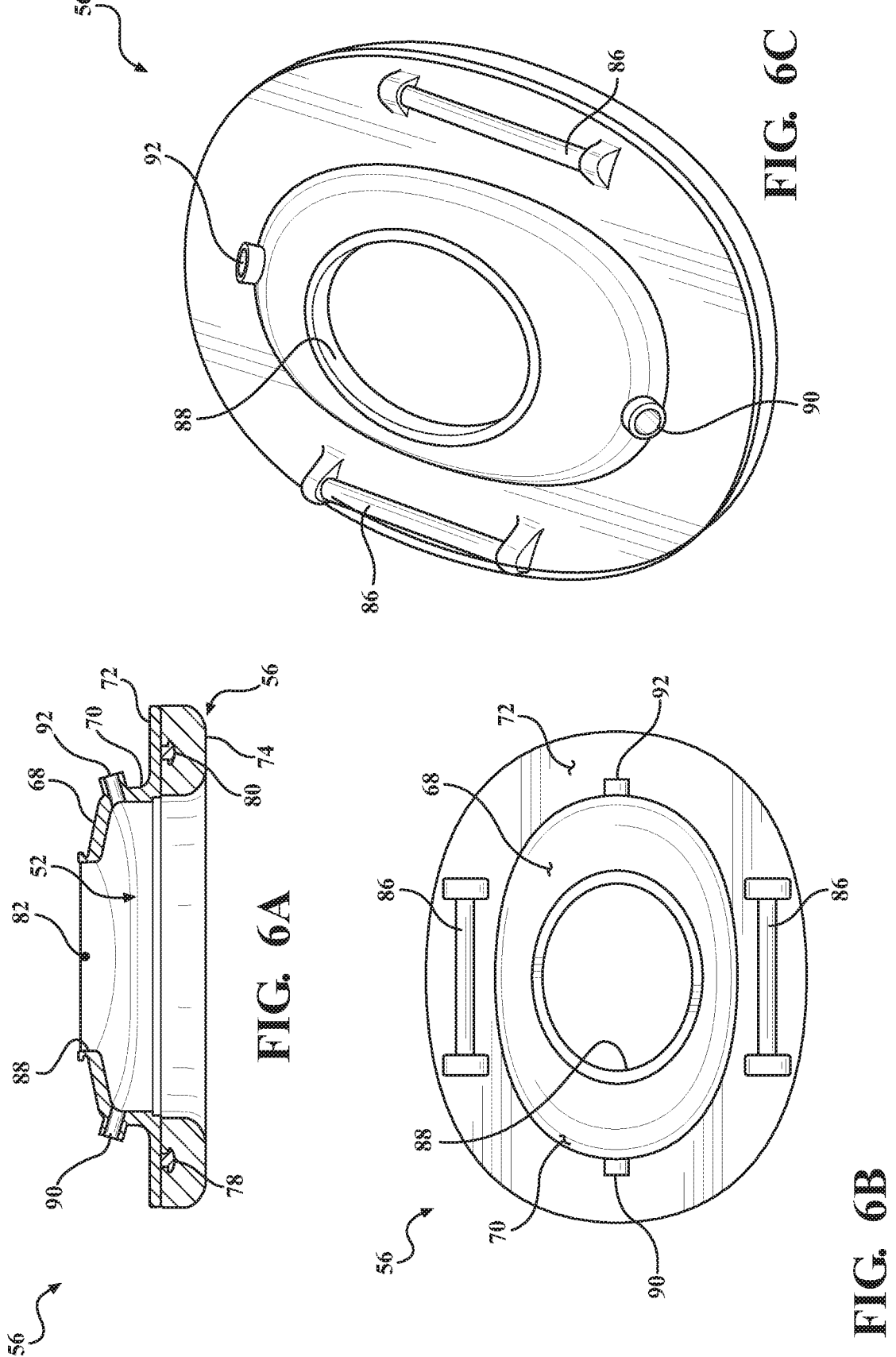
FIG. 6 shows several views of a housing in accordance with another exemplary variation of the present disclosure.
Figures 7A, 7B, 7C:
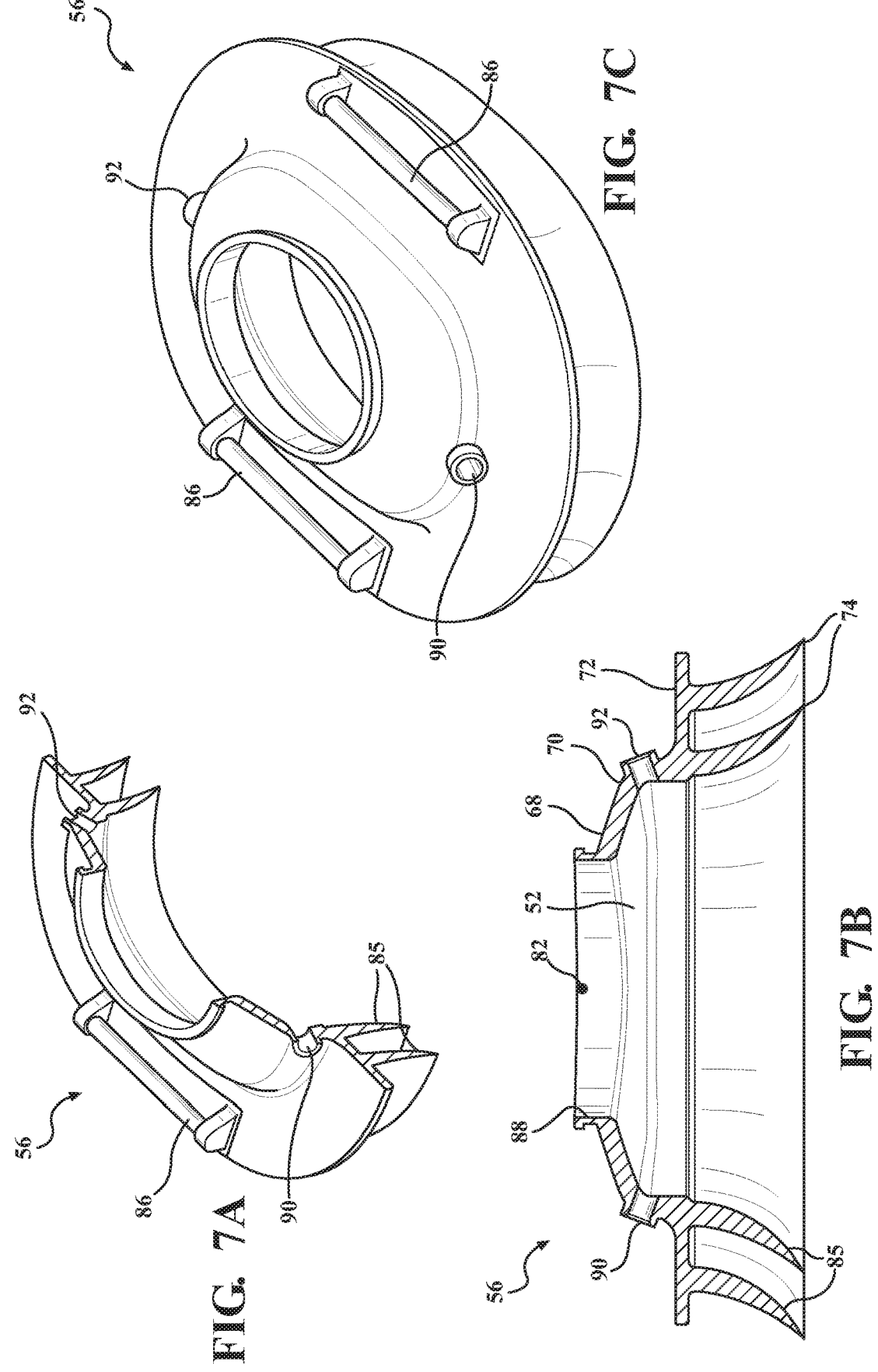
FIG. 7 shows several views of a housing in accordance with still another exemplary variation of the present disclosure.

FIGS. 6 and 7 show the housing 56 in accordance with alternative exemplary variations of the present disclosure. In at least some respects, the housing 56 of the variations to be described is the same as that previously described with like numerals reflecting like structures. For efficiency, only certain aspects of the like structures will be described, but it is understood that similar aspects not described are herein incorporated by reference. FIGS. 6 and 7 show that the superior, lateral, and inferior aspects 68, 70, 72 are of unitary construction. With no discrete upper and lower housings, manufacturing complexity and cost may be simplified and reduced, respectively, and the possibility of fluid leakage at the coupling interface between the upper and lower housings is eliminated. The superior and lateral aspects 68, 70 collectively define the housing 58 that is substantially hemispherical in shape such that the housing 56 substantially encapsulates the auricle. The inferior aspect 72 extends radially outward from the lateral aspect 70. As a result, the fluid reservoir volume 52 is generally defined within the boundary defined by the lateral aspect 70, below the superior aspect 68, and above the opening of the ear. In the present variations, the inferior aspect 72 does not meaningfully define the fluid reservoir volume 52, and rather functions as the structure to which the sealing member 84 is coupled. Thus, the fluid reservoir volume 52 of the variation of FIGS. 2-5 may be relatively larger than those of the variations of FIGS. 6 and 7. It is further noted that FIGS. 6 and 7 show the coupling features 86 coupled to an upper surface of the inferior aspect 72.

With particular reference to FIG. 7, the sealing member 84 includes one or more fins 85 coupled to the housing 56, and more particularly to the inferior aspect 72. The fins 85 are configured to define the sealing surface 74 and provide the fluid-tight seal between the housing 56 and the head of the patient. The fins 85 extend inferiorly from a lower surface of the inferior aspect 72. The fins 85 may be a discrete structure coupled to the inferior aspect 72 or integrally formed with the same. The fins 85 are elongate when viewed in section as shown in FIG. 7. The fins 85 may taper to a point and curve slightly outwardly relative to the axis extending through the pole 82 of the superior aspect 68. The fins 85 may be formed from resilient material such that, when the fins 85 are positioned in abutting relationship the head of the patient, the fins 85 deflect slightly outwardly to define the sealing surface 74. In particular, the curve of the fins 85 induces the fins 85 to deflect slightly outwardly under compression provided to the housing 56 by the retention members 84, such as the elastic band. The resiliency of the fins 85 provides a force against the head of the patient with the resilient force facilitating the fluid-tight seal between the reservoir system 50 and the head of the patient. Further, when the housing 56 is viewed in plan, the fins 85 are generally ring-shaped such that the fins 85 surround the auricle when the housing 56 is coupled to the head of the patient. The fins 85 may be coaxially aligned with the axis extending through the pole 82 of the superior aspect 68. FIG. 7 shows three concentric fins 85, but it is understood that the sealing member 84 may include one, two, or four or more fins. It is further noted that the exemplary variation of the housing 56 shown in FIG. 7 includes the irrigation port 90 and the suction port 92 positioned on opposite sides of the lateral aspect 70 of the housing 56 relative to the axis extending through the pole 82.

Figure 9:
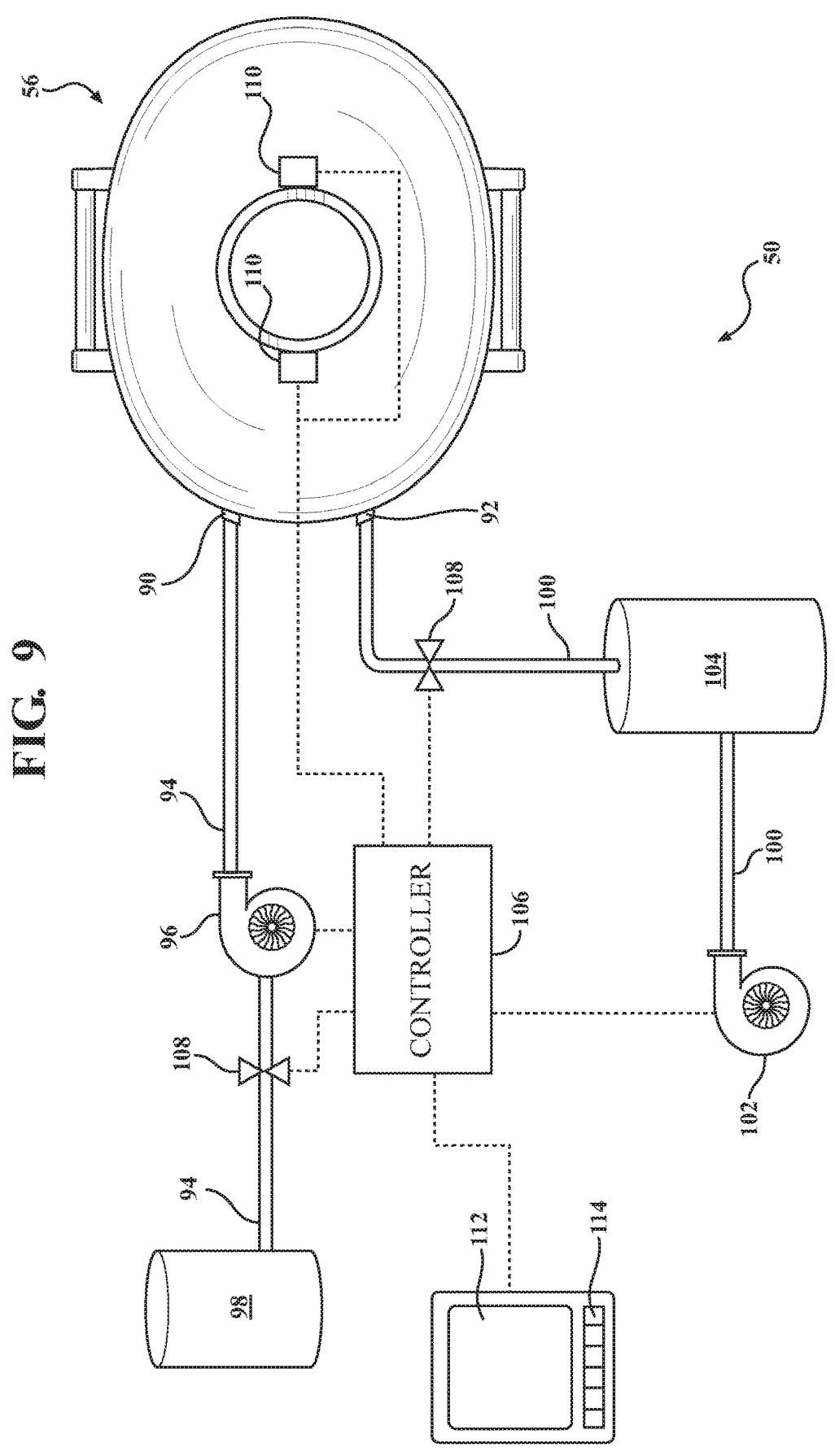
FIG. 9 is a schematic representation of the reservoir system.

Returning to FIGS. 3 and 4, FIG. 3 shows the reservoir system 50 providing the irrigation and the cutting instrument 30 providing the suction; and FIG. 4 shows the cutting instrument 30 providing the irrigation and the suction. In particular, in the illustrated variation of FIG. 3, the cutting instrument 30 includes a suction outlet 34. With further reference to FIG. 9, the suction outlet 34 is configured to be coupled in communication with the suction line 100, the suction source 102, and the disposal reservoir 104. In the illustrated variation of FIG. 4, the cutting instrument 30 includes the suction outlet 34 and an irrigation outlet 35.

In another variation, the endoscope 40 includes an irrigation sheath 41 having an irrigation outlet 35. Suitable irrigation sheaths for endoscopes are described in U.S. Pat. No. 10,028,644, which is hereby incorporated by reference. The irrigation outlet 35 is configured to be coupled in communication with the irrigation line 94, the irrigation pump 96, and the fluid source 98. The suction outlet 34 may be provided on the cutting tool and/or the cutting instrument. In certain variations, the suction outlet 34 and/or the irrigation outlet 35 disposed on the cutting instrument 30 are positioned near the cutting member 32.

Exemplary operation of the variations illustrated in FIGS. 3 and 4 are in many respects similar to those previously described. With the reservoir system 50 of FIG. 3, the housing 56 is coupled to the head of the patient, and the controller 106 operates the irrigation pump 96 to direct the fluid from the fluid source 98 through the irrigation line 94 and the irrigation port 90 within the housing 56. The controller 106 (or a separate controller associated with the cutting instrument 30), operates the suction source 102 to draw suction through the suction outlet 34 and the suction line 100 into the disposal reservoir 104. The irrigation pump 96 and the suction source 102 are operated to maintain the flooded environment 22 in manners previously described. It is appreciated that the irrigation port 90 is positioned above the suction outlet 34 submerged within the flooded environment 22. Thus, the fluid entering the flooded environment 22 through the irrigation port 90 is near, at, or above the fluid level 24, whereas the suction drawn from the flooded environment 22 is below the fluid level 24, and more particularly below the fluid level 24 and within the ear canal. The net effect includes removal of the fluid and debris away from the surgical site with immediate replenishing of the surgical site with "fresh" fluid from above by the force of gravity. Further, with the irrigation port 90 coupled to the housing 56 generally positioned remote from the suction outlet 34 disposed on the cutting instrument 30, the aforementioned swirling effect may further move debris away from the field of view of the endoscope 40. With the reservoir system 50 of FIG. 4, the housing 56 is coupled to the head of the patient, and the controller 106 operates the irrigation pump 96 to direct the fluid from the fluid source 98 through the irrigation line 94 and the irrigation outlet 35. The controller 106 (or a separate controller associated with the cutting instrument 30), operates the suction source 102 to draw suction through the suction outlet 34 and the suction line 100 into the disposal reservoir 104. The irrigation pump 96 and the suction source 102 are operated to maintain the flooded environment 22 in manners previously described. With the fluid being provided to and the suction drawn from the flooded environment 22 below the fluid level 24, and more particularly below the fluid level 24 and within the ear canal, the aforementioned swirling effect may result, and/or an agitation or turbulent effect may be provided at the surgical site that improves cooling effect and/or moves debris away from the field of view of the endoscope 40.

It is further contemplated that in certain variations, the suction port 92 is positioned to function an "overfill outlet." For example, the reservoir system 50 may provide the suction through the suction port 92 and the cutting instrument 30 provides the irrigation. The fluid is provided to the flooded environment 22 through the irrigation outlet 35 below the fluid level 24, and more particularly below the fluid level 24 and within the ear canal, whereas the suction drawn from the flooded environment 22 is near, at, or above the fluid level 24. In another example, the suction port 92 is coupled to the housing 56 and positioned superior to the irrigation port 90 coupled to the housing 56. The fluid is provided to the flooded environment 22 through the irrigation port 90 at a first level, and the suction drawn from the flooded environment 22 through the suction port 92 at a second level different than the first level. If the fluid level 24 is not greater than or equal to the second level, no fluid is drawn through the suction port 92 (and the controller 106 may actuate the suction source 102 to an off state). Once the fluid level 24 reaches the second level, the fluid is drawn through the suction port 92 with the steady state fluid level being maintained at the second level. It is further contemplated that the suction outlet 34 and irrigation outlet 35 disposed on the cutting instrument 30 may be in addition to the irrigation and suction ports 90, 92 disposed on the housing 56. In other words, more than one source of irrigation and/or suction may be provided. The several sources irrigation and suction may be operated in a coordinated manner by the controller 106 to maintain the flooded environment 22 as desired.

It may be advantageous to avoid exposing sensitive portions of the ear anatomy to excessive pressure during the procedure. It is noted that in certain variations, access opening 88 of the housing 56 may open to a surrounding ambient environment, exposing the flooded environment 22 to surrounding atmospheric pressure at the surface of the fluid, and allowing excess pressure to escape the surgical site. Due to the negligible depth of the ear, substantial hydrostatic pressure at the bottom of the ear is not built up from the depth of the fluid above. Therefore, in certain configurations, the hydrostatic pressure within the flooded environment should not substantially differ from the surrounding atmospheric pressure, typically 1.00 atm+/−0.05 atm. Furthermore, a further variation of the disclosure includes configuring the irrigation outlet 35 and irrigation pump 96 such that the irrigation outlet 35 directs fluid into the ear at a substantially atmospheric pressure, ensuring that the pressure in the ear does not exceed 1.00 atm+/−0.05 atm.

Referring to FIG. 10*l*, the subject disclosure also includes an additional method of performing resection within the ear during a surgical procedure through the ear canal. The method comprises the steps of providing a speculum 120 defining a working lumen 121 and a second lumen 122 and placing the speculum 120 within the ear to facilitate access to and visualization of the ear canal through the working lumen 121. Visualization of the ear canal may be achieved through a variety of optical or electronic devices, such as a microscope 126. The method also includes directing a cutting instrument 30 through the working lumen 121 and operating the cutting instrument 30 to resect tissue the ear canal. The method further includes operating an irrigation pump 96 to direct fluid from a fluid source 98 to within the ear canal and operating a suction source 102 to provide suction within the ear canal. At least one of the suction source 102 and the irrigation pump 96 are in fluid communication with the second lumen 122 of the speculum.

Figure 10:
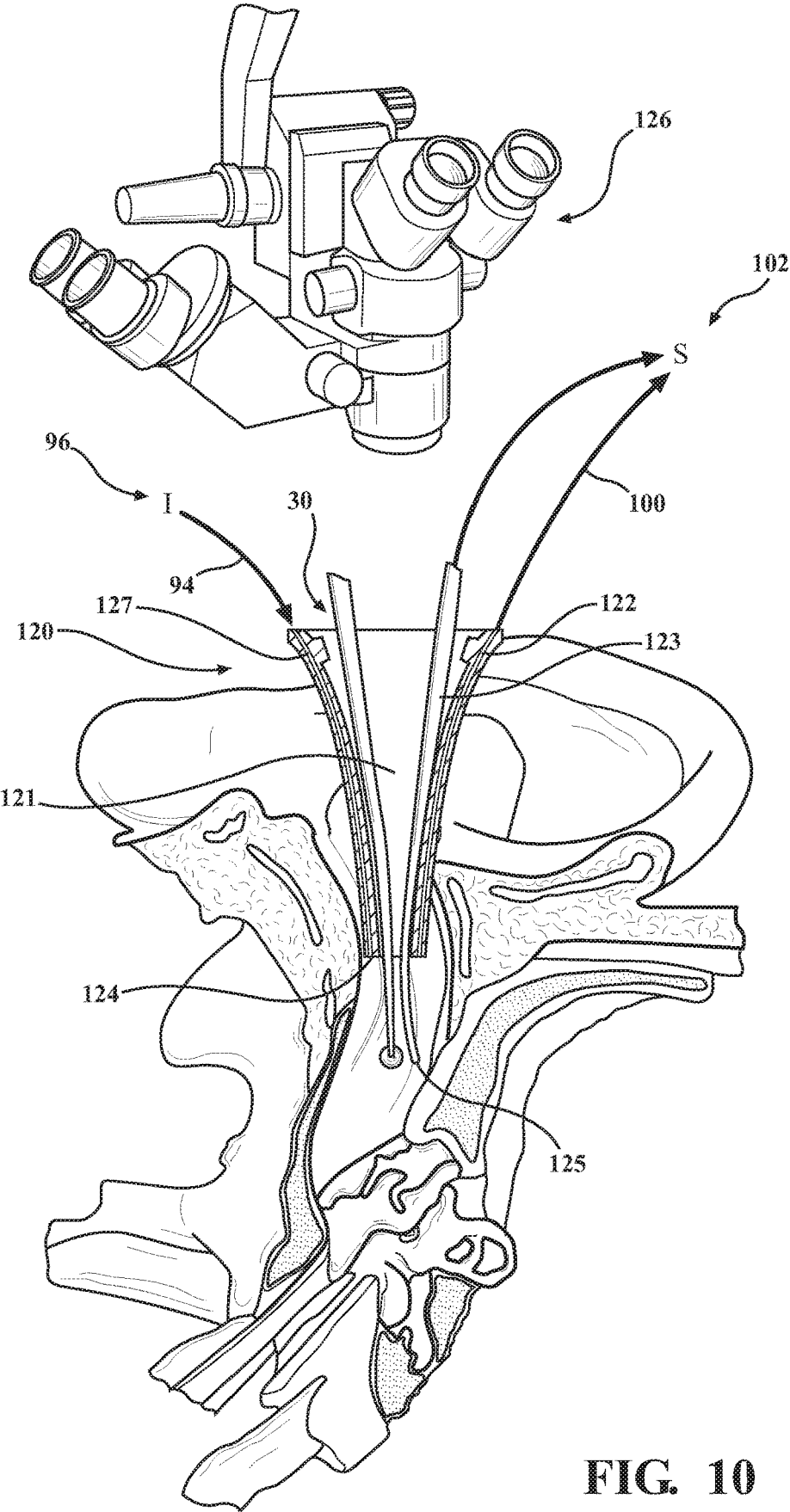
FIG. 10 illustrates an additional variation of the present disclosure with a speculum providing access and visualization to the ear canal.

FIG. 10 illustrates a configuration of the aforementioned additional method of performing resection within the ear during a surgical procedure through the ear canal. It is noted that fluid from the fluid source 98 may be directed to the ear canal by the irrigation pump 96 through the irrigation line 94 and the second lumen 122 of the speculum 120 in fluid communication with the irrigation pump 96, an irrigation outlet 124 of the cutting instrument 30 in fluid communication with the irrigation pump 96, an auxiliary device 123 having an irrigation outlet 124 in fluid communication with the irrigation pump 96, or a combination thereof. Furthermore, suction may be provided to within the ear canal by the suction source 102 through the suction line 100 and the second lumen 122 of the speculum 120 in fluid communication with the suction source 102, an aspiration outlet 125 of the cutting instrument 30 in fluid communication with the suction source 102, an auxiliary device 123 having an aspiration outlet 125 in fluid communication with the suction source 102, or a combination thereof. In a further variation, the speculum may include a third lumen 127 such that the speculum 120 is configured to provide suction and irrigation through the speculum simultaneously using both the second and the third lumens.

As described throughout the present disclosure, the surgical system 20 includes the cutting instrument 30 with the cutting member 32 adapted to resect tissue within the ear. The cutting instrument 30 may include any suitable surgical instrument with a rotatable cutting member 32, including burs, shavers, drills, and the like. Exemplary cutting instruments 30 include the S2 πDrive®, Sumex®, Maestro®, Saber, and Aril drill systems, manufactured by Stryker Corporation (Kalamazoo, Mich.). An exemplary shaver includes the ESSx® microdebrider system and shavers disclosed in commonly owned U.S. Pat. Nos. 6,152,941; 6,689,146; 7,717,931; 8,475,481, each which are hereby incorporated by reference in its entirety. The shaver includes outer tube and a tubular drive shaft rotatably disposed within the outer tube with the cutting member 32 defined between windows within each of the outer tube and the tubular drive shaft. The suction outlet 34 may be in communication with the windows defining the cutting member 32. The windows are adapted to resect the tissue with the cutting instrument 30 rotating the tubular drive shaft. Other suitable cutting instruments 30 may include a router, an electrode for radiofrequency (RF) ablation; a saw or a blade configured to be received by a saw driver, a scalpel, an ultrasonic tip configured to be received by a sonopet, a curette, a rasp, a trocar sleeve, biopsy forceps, ligation devices, tissue staplers, tissue scissors, and/or any other endoscopic cutting device configured to be received by an endo-handpiece.

Figure 11:
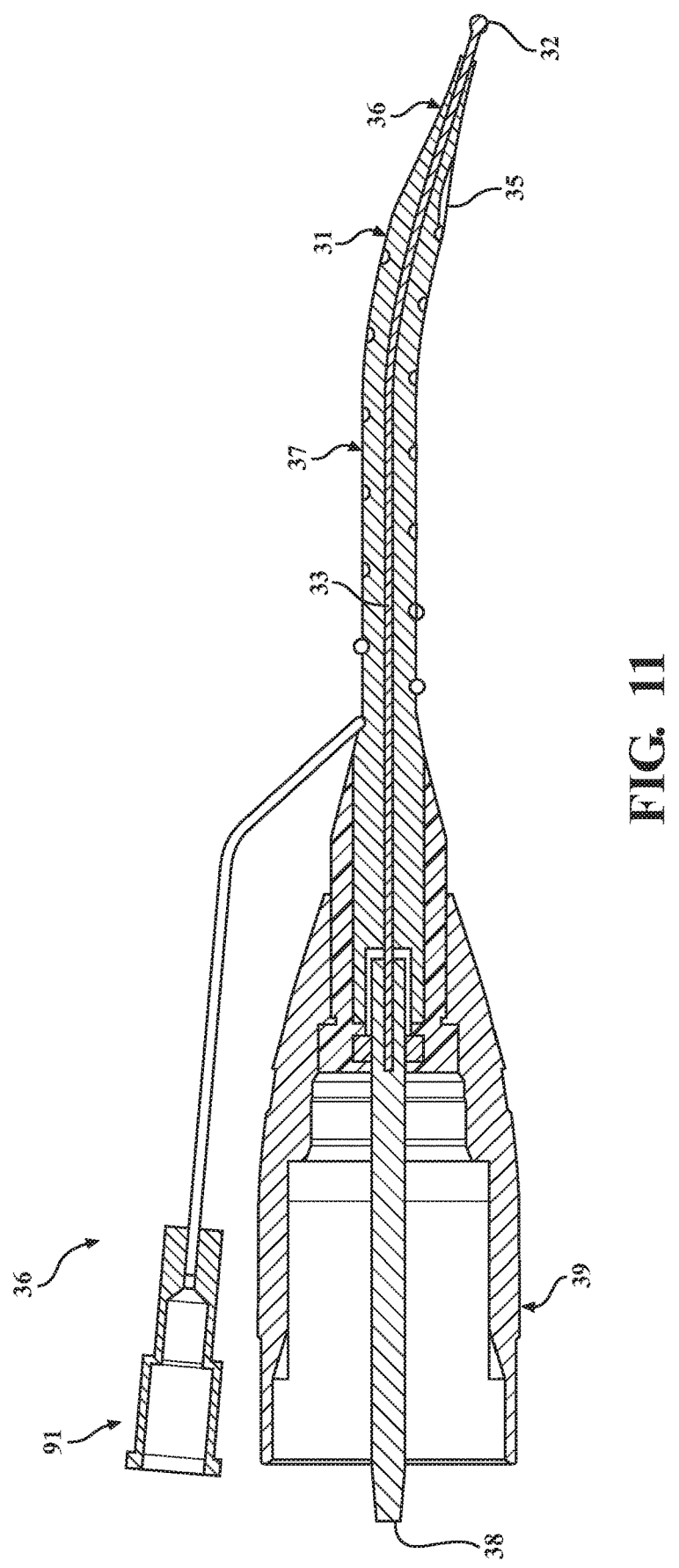
FIG. 11 is a sectional view of an exemplary cutting instrument.

The aforementioned drill and shaver systems may be straight or angled. Of particular interest in the context of transcanal endoscopic ear surgery is the cutting instrument 30 being curved. With reference to FIG. 11, the cutting instrument 30 may further include a nosetube 31 and a drive shaft 33 rotatably disposed within the nosetube 31. The cutting member 32 is disposed at a distal end of the drive shaft 33. The nosetube 31 may include a distal section 36 extending from a proximal section 37. The distal section 36 may be angled or curved relative to the proximal section 37 to define a bend. The drive shaft 33 is flexible, and in certain variations solid and flexible, with the drive shaft 33 rotatably disposed in the distal and proximal sections 36, 37 of the nosetube 31. A proximal end of the drive shaft 33 is coupled to a chuck 38 configured to be removably coupled to a motor (not shown) disposed within a handpiece (not shown). A hub 39 is coupled to and extends proximally from the nosetube 31. The hub 39 is configured to be removably coupled with the handpiece.

The cutting instrument 30 may include the irrigation outlet 35 disposed within the nosetube 31 near the cutting member 32. The irrigation outlet 35 is in communication with a port 91 configured to be coupled with the irrigation line 94 in fluid communication with the irrigation pump 96 and the fluid source 98 (see FIG. 9). Specifics regarding providing irrigation using the cutting instrument 30 illustrated in FIG. 11 are disclosed in commonly owned International Publication No. WO 2016/054140, which is hereby incorporated by reference in its entirety. It is further contemplated that the irrigation may be provided through a lumen (not shown) extending through the nosetube 31. In variations where the cutting instrument 30 is providing the irrigation and the suction, two lumens may extend through the nosetube 31 with one for directing the irrigation and the other for drawing the suction. One of both of the lumens may extend through a distal bushing (not shown) disposed between the nosetube 31 and the drive shaft 33 near the cutting member 32 coupled to the distal end of the drive shaft 33.

The surgical system 20 of the present disclosure including the curved cutting instrument 30 may be used to perform any number of endoscopic procedures through the ear canal. As mentioned, of particular interest is the treatment of cholesteatomas located at the superior aspect of the tympanic cavity near the tympanic membrane. The patient is positioned in the lateral decubitus position as shown in FIG. 8A such that the ear canal is generally oriented vertically to create a gravity well towards the middle ear. The reservoir system 50 is coupled to the head of the patient in manners previously described. One or more navigation markers 116 may be coupled to the patient in a suitable location with the navigation markers detectable by an optical camera in the surgical suite, as described in commonly owned U.S. Pat. No. 9,901,407, hereby incorporated by reference in its entirety. The navigation markers 116 may facilitate the determination an intraoperative position of the cutting member 32 of the cutting instrument 30 within the ear canal. Additionally or alternatively each of the cutting instrument 30 and the endoscope 40 may include components and features of the computer-implemented navigation systems disclosed in commonly owned U.S. Pat. No. 8,657,809 and U.S. Patent Publication Nos. 2014/0135617 and 2014/ 0243658, each of which is hereby incorporated by reference in its entirety. In addition, the reservoir system may include one or more navigation markers.

With the reservoir system 50 coupled to the head of the patient, the flooded environment 22 is provided in manners previously described. The cutting instrument 30, and in certain variations the endoscope 40, are directed into the ear canal with the cutting member 32 being submerged within the flooded environment 22. It is understood that at least a portion of the distal section 36 of the nosetube 31 may also be submerged within the flooded environment 22. The cutting member 32 of the cutting instrument 30 is positioned adjacent the temporal bone while submerged within the flooded environment, and more particularly adjacent the offending cholesteatoma. In one example, the cutting member 32 is positioned adjacent the cholesteatoma associated with the temporal bone lateral to the tympanic membrane and superior to the ear canal. The cutting instrument 30 is operated to rotate the cutting member 32 submerged within the flooded environment 22 to resect the cholesteatoma. Should the offending cholesteatoma be medial the tympanic membrane (i.e., within the tympanic cavity), it may be indicated to resect the tympanic membrane to provide access to the tympanic cavity. The resection of the tympanic membrane may occur before or after providing the flooded environment 22 to the ear. With access provided to the tympanic cavity, the middle ear may flood with the fluid constituting the flooded environment 22. It is understood that the intra-ear pressure may limit or prevent flooding of the middle ear. The cutting member 32 is positioned adjacent the offending cholesteatoma medial to the tympanic membrane and superior to the ear canal, and the cutting instrument 30 is operated to rotate the cutting member 32 to resect the cholesteatoma.

Figure 12:
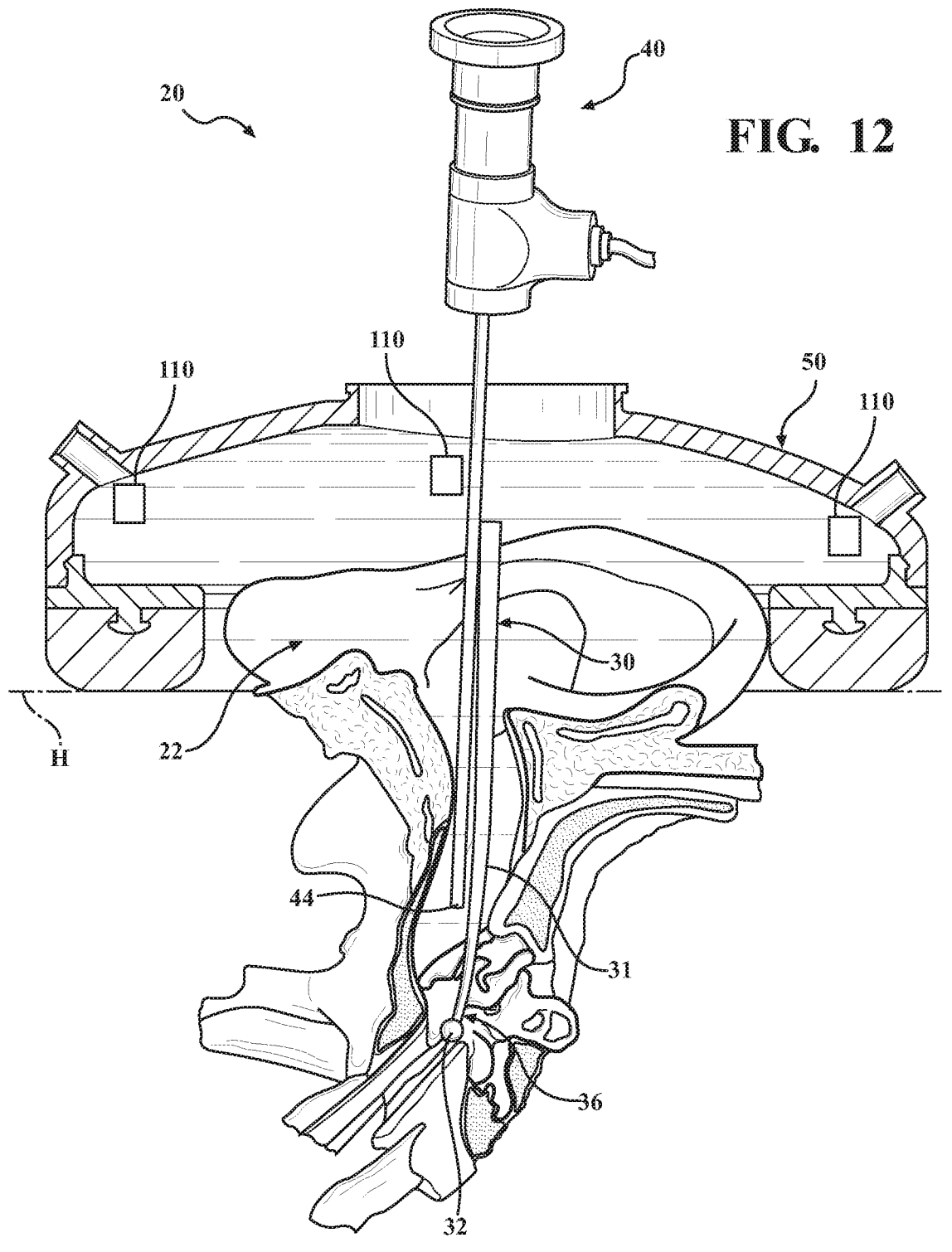
FIG. 12 is an illustration of the surgical system with the reservoir system of FIGS. 2-4 providing the flooded environment within the ear canal to perform a step of an exemplary method of the present disclosure.
Figure 13:
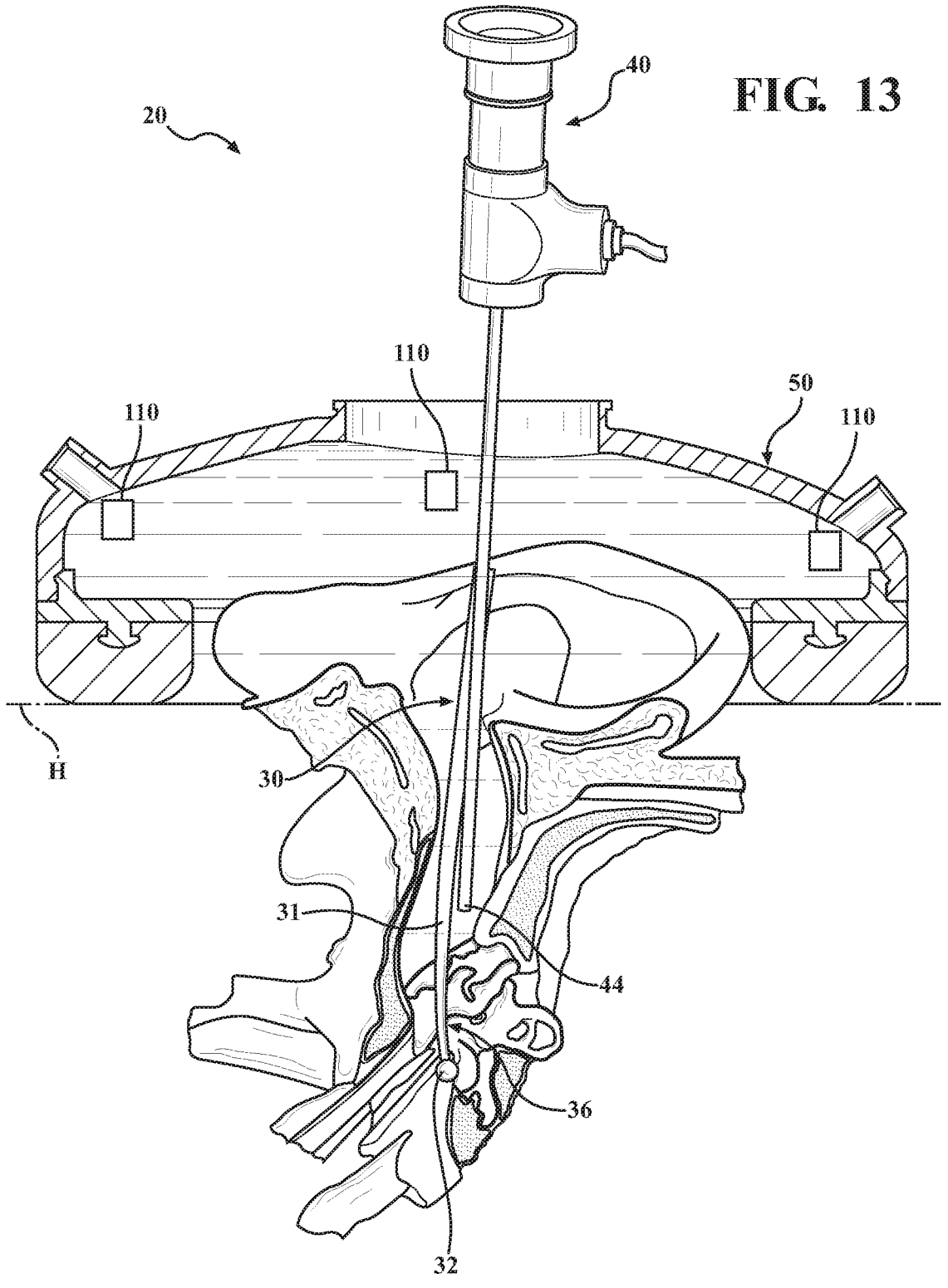
FIG. 13 is an illustration of the surgical system with the reservoir system of FIGS. 2-4 providing the flooded environment within the ear canal to perform another step of the exemplary method.

FIGS. 12 and 13 illustrate further steps of the surgical procedure in which tissue within the middle ear or the inner ear is resected. FIG. 12 shows the cutting member 32 advanced medially within the flooded environment 22 under visualization of the endoscope 40. The distal section 36 of the nosetube 31 is oriented inferiorly. The cutting instrument 30 is operated to rotate the cutting member 32 submerged within the flooded environment to resect the tissue within the middle ear or the inner ear, for example, the temporal bone medial the Eustachian tube and inferior the cochlea. With further reference to FIG. 13, in certain methods the cutting instrument 30 is inverted such that the distal section 36 of the nosetube 31 is oriented superiorly. For example, the cutting instrument 30 is rotated about its longitudinal axis by approximately 180°, for example, between 150° and 210°. The inversion of the distal section 36 of the nosetube 31 may occur without retracting the cutting instrument 30, and further without previous resection of the temporal bone proximal the jugular bulb. Known methods using a curved cutting instrument often require resection of the temporal bone proximal the jugular bulb to provide sufficient clearance for the superiorly oriented distal section of the cutting instrument 30. The cutting instrument 30 of the present disclosure, including the bend between distal and proximal sections 36, 37 having a lesser radius of curvature relative to known systems, provides for inversion of the distal section 36 without retracting the cutting instrument 30 and without resection of the temporal bone proximal the jugular bulb. Greater access is provided to the inner ear, and in particular inferior to the cochlea to resect, for example, the tissue to create a channel to the internal auditory canal. Other methods of performing transcanal endoscopic ear surgery with the benefits providing the flooded environment 22 are contemplated.

Moreover, the aforementioned systems and methods of performing endoscopic surgery within the flooded environment 22 may be well suited for other procedures involving other orifices, cavities and/or canals within the human body, or through openings resected through skin and/or bone of the patient during the surgical procedure. Examples include the flooded environment 22 being provided to the nasal cavity, mouth cavity, or eye cavity. Further examples include the flooded environment 22 being provided to a craniotomy during neurosurgery, a joint cavity during orthopedic surgery, or a soft tissue void space during cardiothoracic surgery.

Additional clauses of the present invention are included in the following numbered paragraphs:

I. A method of performing a surgical procedure within an ear through an ear canal with the ear extending from a head of a patient, the method including the steps of:
directing fluid from a fluid source to within the ear canal;
maintaining a volume of the fluid within the ear canal to provide a flooded environment within the ear canal;
submerging a cutting member of a cutting instrument within the flooded environment with the cutting instrument including a nosetube, a drive shaft rotatably disposed within the nosetube, and the cutting member at a distal end of the drive shaft; and
with the cutting member submerged within the flooded environment, submerging an endoscope within the flooded environment with the flooded environment minimizing obstruction of a field of view of the camera; and
operating the cutting instrument to rotate the cutting member submerged within the flooded environment to resect tissue within the field of view of the endoscope.

II. The method of I, further including coupling a reservoir system to the head to at least partially surround the auricle with the reservoir system including a housing defining a fluid reservoir volume when coupled to the head and including an access opening in fluid communication with the fluid reservoir volume.

III. The method of II, further including supporting the cutting instrument with one hand while submerging the cutting member of the cutting instrument within the flooded environment through the access opening of the reservoir system, and supporting the endoscope with the other hand while submerging the endoscope within the flooded environment through the access opening of the reservoir system.

IV. The method of II or III, wherein the volume of the fluid includes a fluid level, the method further including maintaining the fluid level within the fluid reservoir volume such that an entirety of the ear canal is filled with the fluid to provide the flooded environment.

V. A surgical system for providing a flooded environment within the ear during a surgical procedure through an ear canal with the ear extending from the head of a patient and including an auricle defining an opening into the ear canal, the system including:
a housing adapted to be coupled to the head of the patient and including a lateral aspect defining an opening sized to receive the auricle of the ear, and a superior aspect coupled to the lateral aspect to define a fluid reservoir volume between the lateral and superior aspects for maintaining a volume of the fluid during the surgical procedure, and an access opening within the superior aspect and in fluid communication with the reservoir volume;
an irrigation port within the housing and adapted to be coupled with an irrigation line in fluid communication with a pump and a fluid source;
a cutting instrument positionable through the access opening of the housing and including a rotatable cutting member and a suction port in fluid communication a suction source, wherein the cutting member is adapted to be submerged within the volume of the fluid during the surgical procedure; and a controller adapted to be coupled with the pump and the suction source with the controller configured to operate the pump to provide the fluid from the fluid source through the irrigation port of the housing, and operate the suction source to draw suction through the suction port of the cutting instrument at a suction rate based on the flow rate to maintain the volume of the fluid within the ear canal.

VI. The surgical system of V, further including an endoscope positionable through the access opening of the housing to be submerged within the volume of the fluid.

VII. The surgical system of VI, wherein the access opening is sized to simultaneously receive the endoscope and the cutting instrument.

VIII. The surgical system of any of V-VII, wherein the cutting instrument further includes a nosetube, a solid drive shaft rotatably disposed within the nosetube with the cutting member at a distal end of the solid drive shaft.

IX. The system of VIII, wherein the nosetube includes a distal section angled relative to a proximal section, and the drive shaft includes a flexible drive shaft rotatably disposed within the proximal and distal sections to define a curved cutting instrument.

X. The surgical system of any of V-VII, wherein the cutting instrument further includes an outer tube, a tubular drive shaft rotatably disposed within the nosetube, and a cutting member defined between windows within each of the outer tube and the tubular drive shaft.

XI. The surgical system of any of V-IX, further including a sealing surface adapted to be positioned in abutting relationship with the head about the auricle to provide a fluid-tight seal.

XII. The surgical system of XI, further including a sealing member coupled to the housing and defining the sealing surface.

XIII. A surgical system for provided a flooded environment within the ear during a surgical procedure through an ear canal, the system including:
    a cutting instrument including a rotatable cutting member, an irrigation outlet adapted to be in fluid communication with a pump, and a suction outlet adapted to be in fluid communication a suction source; and
    a controller adapted to be coupled with the pump and the suction source with the controller configured to operate the pump to provide the fluid from the fluid source through the irrigation outlet of the cutting instrument, and operate the suction source to draw suction through the suction outlet of the cutting instrument at a suction rate based on the flow rate to maintain the flooded environment of the fluid within the ear canal as the cutting member is submerged within the flooded environment during the surgical procedure.

XIV. A surgical system for providing a flooded environment within the ear during a surgical procedure through an ear canal with the ear extending from the head of a patient and including an auricle defining an opening into the ear canal, the system including:
    a housing adapted to be coupled to the head of the patient and including a lateral aspect defining an opening sized to receive the auricle of the ear, and a superior aspect coupled to the lateral aspect to define a fluid reservoir volume between the lateral and superior aspects for maintaining a volume of the fluid during the surgical procedure, an access opening within the superior aspect and in fluid communication with the reservoir volume, and a suction port disposed on the housing having a suction line in fluid communication with a suction source;
    an endoscope having an irrigation sheath having an irrigation outlet and adapted to be coupled with an irrigation line in fluid communication with a pump and a fluid source;
    a cutting instrument positionable through the access opening of the housing and including a rotatable cutting member wherein the cutting member is adapted to be submerged within the volume of the fluid during the surgical procedure; and
    a controller adapted to be coupled with the irrigation pump and the suction source with the controller configured to operate the irrigation pump to provide the fluid from the fluid source through the irrigation outlet of the endoscope, and operate the suction source to draw suction through the suction port of the housing at a suction rate based on the flow rate to maintain the volume of the fluid within the ear canal.

XV. A surgical system for performing resection within the ear during a surgical procedure through an ear canal with the ear extending from the head of a patient and including an auricle defining an opening into the ear canal, the system including:
    a speculum defining a working lumen and a second lumen;
    a cutting instrument including a rotatable cutting member positionable through the working lumen;
    an irrigation pump for directing a fluid from a fluid source to the ear canal;
    a suction source for providing suction within the ear canal, wherein one of the suction source and the irrigation pump are in fluid communication with the second lumen;
    a controller adapted to be coupled with the irrigation pump and the suction source with the controller configured to operate the pump to provide the fluid from the fluid source through the second lumen of the speculum, operate the suction source to draw suction through the second lumen of the speculum, or a combination thereof.

XVI. A method for provided a flooded environment within the ear during a surgical procedure through an ear canal with the ear extending from the head of a patient and including an auricle defining an opening into the ear canal, the system including:
    providing a reservoir system including a housing, an access opening within the housing, an irrigation port within the housing in fluid communication with a pump and a fluid source, a suction port within to the housing and in fluid communication with a suction source;
    positioning the patient in a lateral decubitus position;
    coupling the reservoir system to the head of the patient to at least partially surround the auricle and define a fluid reservoir volume with the access opening in communication with the fluid reservoir volume;
    operating the pump to direct fluid from the fluid source through the irrigation port to within ear canal at a flow rate;
    operating the suction source to provide suction to the flooded environment through the suction port at a suction rate based on the flow rate to maintain the volume of the fluid within the ear canal and the fluid reservoir volume such that an entirety of the ear canal is filled with the fluid to provide the flooded environment within the ear canal;

directing a cutting instrument through the access opening within the housing; and operating the cutting instrument to resect tissue within the ear.

XVII. A method for provided a flooded environment within the ear during a surgical procedure through an ear canal with the ear extending from the head of a patient and including an auricle defining an opening into the ear canal, the system including:

providing a reservoir system including a housing, an access opening within the housing, and an irrigation port within the housing in fluid communication with a pump and a fluid source;

providing a cutting instrument including a suction outlet in fluid communication with a suction source;

positioning the patient in a lateral decubitus position;

coupling the reservoir system to the head of the patient to at least partially surround the auricle and define a fluid reservoir volume with the access opening in communication with the fluid reservoir volume;

operating the pump to direct fluid from the fluid source through the irrigation port to within ear canal at a flow rate;

operating the suction source to provide suction to the flooded environment through the suction outlet at a suction rate based on the flow rate to maintain the volume of the fluid within the ear canal and the fluid reservoir volume such that an entirety of the ear canal is filled with the fluid to provide the flooded environment within the ear canal;

directing a cutting instrument through the access opening within the housing; and operating the cutting instrument to resect tissue within the ear.

XVIII. A method for provided a flooded environment within the ear during a surgical procedure through an ear canal with the ear extending from the head of a patient and including an auricle defining an opening into the ear canal, the system including:

providing a reservoir system including a housing and an access opening within the housing;

providing a cutting instrument including an irrigation outlet in fluid communication with a pump and a fluid source, and a suction outlet in fluid communication with a suction source;

positioning the patient in a lateral decubitus position;

coupling the reservoir system to the head of the patient to at least partially surround the auricle and define a fluid reservoir volume with the access opening in communication with the fluid reservoir volume;

operating the pump to direct fluid from the fluid source through the irrigation outlet to within ear canal at a flow rate;

operating the suction source to provide suction to the flooded environment through the suction outlet at a suction rate based on the flow rate to maintain the volume of the fluid within the ear canal and the fluid reservoir volume such that an entirety of the ear canal is filled with the fluid to provide the flooded environment within the ear canal;

directing a cutting instrument through the access opening within the housing; and operating the cutting instrument to resect tissue within the ear.

Several variations have been discussed in the foregoing description. However, the variations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method of performing a surgical procedure within an ear through an ear canal with the ear canal extending from a head of a patient and including an inner ear with a cochlea, a middle ear with a tympanic cavity, an outer ear with an auricle defining an opening into the ear canal separated from the middle ear with a tympanic membrane, and temporal bone surrounding portions of the ear, said method comprising the steps of:

operating an irrigation pump to direct fluid from a fluid source to the ear canal such that a volume of fluid within the ear canal provides a flooded environment within the ear canal, wherein the flooded environment is open to ambient environment;

sensing a level of the fluid within the flooded environment with one or more sensors, the level of fluid defined by a location of a surface of the volume of fluid;

transmitting a fluid level signal based on the level of fluid sensed by the one or more sensors to a controller in communication with the irrigation pump;

maintaining the volume of the fluid within the ear canal by adjusting a flow rate of the fluid provided from the fluid source to the ear canal by the irrigation pump with the controller based on the fluid level signal;

submerging a rotatable cutting member of a cutting instrument within the flooded environment; and operating the cutting instrument to rotate the cutting member while the cutting member is submerged within the flooded environment to resect tissue within the ear.

2. The method of claim 1, wherein the step of maintaining the volume of the fluid within the ear canal further comprises maintaining a steady state volume of the fluid within the ear canal.

3. The method of claim 2, further comprising providing suction to the flooded environment at a suction rate substantially equal to the flow rate.

4. The method of claim 3, wherein the steps of providing the fluid and providing suction are performed simultaneously and continuously during the surgical procedure.

5. The method of claim 1, wherein the volume of the fluid includes the fluid level, said method further comprising maintaining the fluid level by adjusting a flow rate of the fluid provided from the fluid source to the ear canal by the irrigation pump with the controller based on the fluid level signal such that an entirety of the ear canal is filled with the fluid to provide the flooded environment.

6. The method of claim 1, further comprising submerging an endoscope within the flooded environment with the flooded environment minimizing obstruction of a field of view of the endoscope.

7. The method of claim 1, further comprising coupling a reservoir system to the head of the patient to at least partially surround the auricle with the reservoir system comprising a housing defining a fluid reservoir volume when coupled to the head and comprising an access opening in fluid communication with the fluid reservoir volume.

8. The method of claim 7, wherein the step of maintaining the volume of the fluid within the ear canal comprises adjusting a flow rate of the fluid provided from the fluid source to the ear canal by the irrigation pump with the controller based on the fluid level signal such that an entirety of the ear canal is filled with the fluid to provide the flooded environment.

9. The method of claim 7, further comprising directing the cutting member of the cutting instrument within the flooded environment through the access opening of the reservoir system.

10. The method of claim 7, further comprising directing an endoscope within the flooded environment through the access opening of the reservoir system.

11. A method for providing a flooded environment within an ear during a surgical procedure through an ear canal with the ear extending from a head of a patient and including an auricle defining an opening into the ear canal, said method comprising the steps of:

provided a reservoir system comprising a housing, an access opening within the housing, and an irrigation port within the housing and in fluid communication with an irrigation pump and a fluid source;

coupling the reservoir system to the head of the patient to at least partially surround the auricle and define a fluid reservoir volume with the access opening in communication with the fluid reservoir volume;

operating the irrigation pump to direct fluid from the fluid source through the irrigation port to within the ear canal such that a volume of fluid within the ear canal and above the auricle of the ear provides a flooded environment within the ear canal and fluid reservoir volume wherein the flooded environment is open to ambient environment;

sensing a level of the fluid within the fluid reservoir volume with one or more sensors coupled to the housing, wherein the level of fluid is defined by a location of a surface of the volume of fluid;

transmitting a fluid level signal based on the level of fluid within the fluid reservoir volume sensed by the one or more sensors to a controller in communication with the irrigation pump;

maintaining the volume of the fluid within the fluid reservoir volume by adjusting a flow rate of the fluid provided by the irrigation pump with the controller based on the fluid level signal;

directing a cutting instrument through the access opening within the housing; and operating the cutting instrument to resect tissue within the ear in the flooded environment.

12. The method of claim 11, further comprising submerging a cutting member of the cutting instrument within the flooded environment prior to resecting the tissue within the ear.

13. The method of claim 11, further comprising directing an endoscope within the flooded environment through the access opening of the reservoir system while the cutting instrument is positioned within the access opening.

14. The method of claim 13, wherein the endoscope further comprises an irrigation sheath having an irrigation outlet in fluid communication with the irrigation pump to direct fluid from the fluid source to the ear canal.

15. The method of claim 11, further comprising providing a fluid-tight seal between the reservoir system and the head of the patient.

16. The method of claim 11, wherein the reservoir system further comprises a suction port within the housing and in fluid communication with a suction source, said method further comprising the step of operating the suction source to provide suction to the flooded environment through the suction port at a suction rate based on the flow rate to maintain the volume of the fluid within the ear canal.

17. The method of claim 11, wherein the cutting instrument includes a suction port in fluid communication with a suction source, said method further comprising the step of operating the suction source to provide suction to the flooded environment through the suction port at a suction rate based on the flow rate to maintain the volume of the fluid.

* * * * *